United States Patent
Pollak et al.

(10) Patent No.: US 12,110,553 B2
(45) Date of Patent: *Oct. 8, 2024

(54) METHODS FOR DIAGNOSING AND ASSESSING RISK OF DEVELOPING GLOMERULOSCLEROSIS

(71) Applicants: The Brigham and Women's Hospital, Inc., Boston, MA (US); Children's Medical Center Corporation, Boston, MA (US)

(72) Inventors: Martin Pollak, Brookline, MA (US); Elizabeth J. Brown, Dallas, TX (US); Johannes Schlondorff, Chestnut Hill, MA (US)

(73) Assignees: The Brigham and Women's Hospital, Inc., Boston, MA (US); Children's Medical Center Corporation, Boston, MA (US)

(*) Notice: Subject to any disclaimer, the term of this patent is extended or adjusted under 35 U.S.C. 154(b) by 542 days.

This patent is subject to a terminal disclaimer.

(21) Appl. No.: 17/113,957

(22) Filed: Dec. 7, 2020

(65) Prior Publication Data

US 2021/0198740 A1 Jul. 1, 2021

Related U.S. Application Data

(63) Continuation of application No. 15/297,804, filed on Oct. 19, 2016, now Pat. No. 10,858,705, which is a continuation of application No. 13/513,447, filed as application No. PCT/US2010/059316 on Dec. 7, 2010, now Pat. No. 9,499,867.

(60) Provisional application No. 61/267,313, filed on Dec. 7, 2009.

(51) Int. Cl.
| | | |
|---|---|---|
| *C12Q 1/68* | (2018.01) | |
| *C12Q 1/6811* | (2018.01) | |
| *C12Q 1/6813* | (2018.01) | |
| *C12Q 1/6816* | (2018.01) | |
| *C12Q 1/6827* | (2018.01) | |
| *C12Q 1/6876* | (2018.01) | |
| *C12Q 1/6883* | (2018.01) | |
| *G01N 33/68* | (2006.01) | |
| *C12Q 1/6886* | (2018.01) | |

(52) U.S. Cl.
CPC ............ *C12Q 1/6883* (2013.01); *C12Q 1/68* (2013.01); *C12Q 1/6811* (2013.01); *C12Q 1/6813* (2013.01); *C12Q 1/6816* (2013.01); *C12Q 1/6827* (2013.01); *C12Q 1/6876* (2013.01); *G01N 33/6854* (2013.01); *G01N 33/6893* (2013.01); *C12Q 1/6886* (2013.01); *C12Q 2600/106* (2013.01); *C12Q 2600/118* (2013.01); *C12Q 2600/156* (2013.01); *C12Q 2600/158* (2013.01); *C12Q 2600/16* (2013.01); *G01N 2800/347* (2013.01)

(58) Field of Classification Search
None
See application file for complete search history.

(56) References Cited

U.S. PATENT DOCUMENTS

| | | |
|---|---|---|
| 5,238,924 A | 8/1993 | Smith |
| 5,525,464 A | 6/1996 | Drmanac et al. |
| 6,239,120 B1 | 5/2001 | Hallgren et al. |
| 9,499,867 B2 | 11/2016 | Pollak |
| 10,858,705 B2 * | 12/2020 | Pollak ................. C12Q 1/6816 |
| 2003/0073623 A1 | 4/2003 | Drmanac |

OTHER PUBLICATIONS

"Genetic Testing," available online at http://medical-dictionary.thefreedictionary.com/ Genetic+analysis, p. 3, 1st full paragraph (2014).
Akiyama et al., Actin-related protein 3 (Arp3) is mutated in proteinuric BUF/Mna rats; Mamm. Genome; 2008; 19(1):41-50.
*Ariosa Diagnostics, Inc. v. Sequenom, Inc.*, 788 F.3d 1371 (Fed. Cir. 2015).
BLAST comparison between Drmanac's SEQ Id No. 23,534 and claimed SEQ Id No. 21, 2018, 2 pages.
Brown et al., Mutations in the formin protein INF2 cause focal segmental glomerulosclerosis,; Nature Genetics; 2009; 42(1):72-76.
Chhabra et al., "INF2 Is a WASP homology 2 motif-containing formin that severs actin filaments and accelerates both polymerization and depolymerization," J. Biol. Chem.; 2006: 281:26754-26767.
Chhabra et al., "INF2 is an endoplasmic reticulum-associated formin protein," J. Cell Sci.; 2009; 122:1430-1440.
D'Agati et al., "Pathologic classification of focal segmental glomerulosclerosis: a working proposal," Am. J. Kidney Dis.; 2004; 43:368-382.
Dai et al., "ACTN4 gene mutations and single nucleotide polymorphisms in idiopathic focal segmental glomerulosclerosis," Nephron: Clinical Practice; 2009; 111(2):87-94.
Deegans et al., "Review on diagnosis and treatment of focal segmental glomerulosclerosis," Neth. J. Nd. 66:3-12 (2008).
SEQ Id No. 23,534 of Drmanac et al., US2003/0073623 A1, (2003).
Evans et al., "Pharmacogenomics: Translating Functional Genomics into Rational Therapeutics," Science 286:487-491 (1999).
Faix et al., "Staying in shape with formins," Dev. Cell; 2006; 10:693-706.
Faul et al., "Actin up: regulation of podocyte structure and function by components of the actin cytoskeleton," Trends Cell Biol.; 2007; 17:428-437.

(Continued)

*Primary Examiner* — Thea D'Ambrosio
(74) *Attorney, Agent, or Firm* — Fish & Richardson P.C.

(57) ABSTRACT

This document features method related to variants in the Inverted Formin 2 (INF2) gene that are associated with susceptibility to focal segmental glomerulosclerosis (FSGS). For example, methods of using such variants for risk assessment and for diagnosing and optimizing treatment of FSGS are provided.

12 Claims, 14 Drawing Sheets

Specification includes a Sequence Listing.

(56) References Cited

OTHER PUBLICATIONS

He et al., "Empirical Establishment of Oligonucleotide Probe Design Criteria," Appl. Environ. Microbiol, 2005, 71:3753-3760.
Hegele, "SNP Judgments and Freedom of Association," Arteoscl. Thromb. Vase. Biol. 22:1058-1061 (2002).
Higgs et al., "Formin proteins: a domain-based approach," Trends Biochem. Sci.; 2005; 30:342-353.
Huber et al., The slit diaphragm: a signaling platform to regulate podocyte function,: Curr. Opin. Nephrol. Hypertens.; 2005; 14:211-216.
PCT International Search Report and Written Opinion; Kim, Ji Yun; Jul. 29, 2011; World Intellectual Property Organization (WIPO) (International Bureau of); PCT/US2010/059316; 11 pages.
Kelley et al., "Protein structure prediction on the Web: a case study using the Phyre server," Nat. Protoc.; 2009; 4:363-371.
Kopp et al., "MYH9 is a major-effect risk gene for focal segmental glomerulosclerosis," Nat. Genet.; 2008; 40(10):1175-1184.
Lee et al., "Variable renal phenotype in a family with an INF2 mutation," Pediatric Nephrology; 2010; 26(1):73-76.
Munkert et al., "Characterization of the transcriptional regulation of the human MT1-MMP gene and association of risk reduction for focal-segmental glomerulosclerosis with two functional promoter SNPs," Nephrology, Dialysis, and Transplantation; 2008; 24(3):735-742.
Orloff et al., "Variants in the Wilms' tumor gene are associated with focal segmental glomerulosclerosis in the African American population," Physiological Genomics; 2005; 21(2):212-221.
Rose et al., "Structural and mechanistic insights into the interaction between Rho and mammalian Dia," Nature: 2005; 435:513-518.
Wakai et al., "A novel method of identifying genetic mutations using an electrochemical DNA array," Nucl. Acids Res, 2004, 32:e141.
Wiley-Blackwell, "Direct Sequencing of DNA, RNA Using Novel Technique," ScienceDaily, available on line at www.sciencedaily.com/releases/2008/01/080128113219.htm, 1 page (2008).
Wu et al., *Handbook of Molecular and Cellular Methods in Biology and Medicine*, 2nd Ed., Cseke et al., eds., CRC Press, pp. 1-20 (2004).

* cited by examiner

```
                                                       FGEP (L42P)
                    FGGN (A13T)                             P
                         T
FSGS
HUMAN    (SEQ ID NO: 32)   1 MSVK-EGAQRKWAALKEKLGP--QDSD--PTEANLESADPELCTRLLQMPSVVNYSGLRKRL
CHIMP    (SEQ ID NO: 32)   1 MSVK-EGAQRKWAALKEKLGP--QDSD--PTEANLESADPELCTRLLQMPSVVNYSGLRKRL
MOUSE    (SEQ ID NO: 33)   1 MSVK-EGAQRKWAALKEKLGP--QDSD--PTEANLESAEPELCIRLLQMPSVVNYSGLRKRL
RAT      (SEQ ID NO: 33)   1 MSVK-EGAQRKWAALKEKLGP--QDSD--PTEANLESAEPELCIRLLQMPSVVNYSGLRKRL
OPOSSUM  (SEQ ID NO: 34)   1 MSVK-EGVQKKWAALKEKLGP--QDSD--PTEANLENAEPELCIRLLQMPSVVNYSGLRKRL
ZEBRAFISH(SEQ ID NO: 35)   1 MSMKAEGAQQKWAAVRGRLGSSQDSDGPQEANLENADAELCTRLLQVPSVVNYSGLRKRL

FGEF,FGFG (R214H)
                                                    FGEA (R218W)
                                                    FGJN (R218Q)
                                                     FSB (E220K)
                                                     H  W K
                                                        Q
            FGGY (E184K)
            FGBR,FGER (S186P)
                 P
                       FGDM (L198R)
                          R
            K     P
FSGS
HUMAN    (SEQ ID NO: 36) 176 YRFSIVMNEILSGSDNVPYTVTLLSVINAVILGPEDLRATQLRNEFIGLQLLDVLARLRD
CHIMP    (SEQ ID NO: 37) 176 YRFSIVMNEILSGSDNVPYTVTLLSVINAVILGPEDLRVTQLRNEFIGLQLLDVLARLRD
MOUSE    (SEQ ID NO: 38) 176 YRFSVIMSELSDSDNVPYTVTLLSVINAIILGPEDLRSRAQIRSEFIGLQLLDILTRLRD
RAT      (SEQ ID NO: 39) 176 YRFSVIMSELSDSDNVPYTVTLLSVINAIILGPEDLRSQAQIRSEFIGLQLLDILTRLRD
OPOSSUM  (SEQ ID NO: 40) 176 YRFSVIMSELSSTDNVPYIITTLSVINAIILGTEELRATQLRNEFIGLQLLDILTKLRD
ZEBRAFISH(SEQ ID NO: 41) 181 YRFSVIMSELSSTDNVPYMVTLLSVINALIFSADGLQQRDKMRKEFIGLQLLEKLRE

ATGTCGGTGAAGGAGGGCGCACAGCGCAAGTGGGCAGCGCTGAAGGAGAAGCTGGGGCCACAGG

ATTCGGACCCCACGGAGGCCAACCTGGAGAGCGCGGACCCCGAGCTGTGCATCCGGCTGCTCCA
                                                     ‾‾‾‾‾‾‾‾‾‾‾‾‾‾
                                                          NO:8

GATGCCCTCTGTGGTCAACTACTCCGGCCTGCGCAAGCGCCTGGAGGGCAGCGACGGCGGCTGG
‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾‾

ATGGTGCAGTTCCTGGAGCAGAGCGGCCTGGACCTGCTGCTGGAGGCGCTGGCGCGGCTGTCGG
GCCGCGGCGTTGCACGTATCTCCGACGCCCTGCTGCAGCTCACCTGCGTCAGCTGCGTGCGCGC
CGTCATGAACTCGCGGCAGGGCATCGAGTACATCCTCAGCAACCAGGGCTACGTGCGCCAGCTC
TCCCAGGCCCTGGACACATCCAACGTGATGGTGAAGAAGCAGGTGTTTGAGCTACTGGCTGCCC
TGTGCATCTACTCTCCCGAGGGCCACGTGCTGACCCTGGACGCCCTGGACCACTACAAGACGGT
                              ‾‾‾‾‾‾‾‾‾‾‾‾‾‾‾‾‾‾‾‾‾‾‾‾‾‾‾‾
                                          NO:5
GTGCAGCCAGCAGTACCGCTTCAGCATTGTCATGAACGAGCTCTCCGGCAGCGACAACGTGCCC
                                       ‾‾‾‾‾‾‾‾‾‾‾‾‾‾‾‾‾‾‾‾‾‾‾‾‾‾‾‾‾
                                                    NO:4

TACGTGGTCACCCTGCTTAGCGTGATCAACGCCGTCATCTTGGGCCCCGAGGACCTGCGCGCGC
‾‾‾‾‾‾‾‾‾‾‾‾‾‾‾‾‾‾‾‾‾‾‾‾‾‾‾                                ‾‾‾‾‾‾‾‾
           NO:1                                              NO:3

NOS:2 & 6
     ‾‾‾‾‾‾‾‾‾‾‾‾‾‾‾‾‾‾‾‾‾‾‾‾‾
GCACCCAGCTGCGGAACGAGTTTATCGGGCTGCAGCTGCTGGACGTCCTGGCTCGCCTGCGAGA
‾‾‾‾‾
NO:7

CCTGGAGGATGCCGACCTGCTGATCCAGCTGGAGGCTTTCGAGGAGGCTAAGGCCGAGGACGAG
GAGGAGCTGCTGCGAGTCTCTGGCGGGGTCGACATGAGCAGCCA     (SEQ ID NO:9)

```
  1 msvkegaqrk waalkeklgp qdsdpteanl esadpelcir lXqmpsvvny sglrkrlegs
 61 dggwmvqfle qsgldlllea larlsgrgva risdallqlt cvscvravmn srqgieyils
121 nqgyvrqlsq aldtsnvmvk kqvfellaal ciyspeghvl tldaldhykt vcsqqyrfsi
181 vmnXlXgsdn vpyvvtlXsv inavilgped lraXtqlXnX figlqlldvl arlrdledad
241 lliqleafee akaedeeell rvsggvdmss hqevfaslfh kvscspvsaq llsvlqgilh
301 leptlrssql lwealeslvn ravllasdaq ectleevver llsvkgrprp splvkahksv
361 qanldqsqrg sspqntttpk psvegqqpaa aaacep

```
   1 cgccccgcgc cgccaggag ccaccgtccg agccttgcgg agcgcggcag tgggcgccgg
  61 ctgcccgcag ccctgaccc ggccccggac ggagcgccgg ccgcaccacc gccctctggc
 121 cgttgcctca ccggctcggc aagatgtcgg tgaaggaggg cgcacagcgc aagtgggcag
 181 cgctgaagga gaagctgggg ccacaggatt cggaccccac ggaggccaac ctggagagcg
 241 cggaccccga gctgtgcatc cggctgcXcc agatgccctc tgtggtcaac tactccggcc
 301 tgcgcaagcg cctggagggc agcgacggcg gctggatggt gcagttcctg gagcagagcg
 361 gcctggacct gctgctggag gcgctggcgc ggctgtcggg ccgcggcgtt gcacgtatct
 421 ccgacgccct gctgcagctc acctgcgtca gctgcgtgcg cgccgtcatg aactcgcggc
 481 agggcatcga gtacatcctc agcaaccagg gctacgtgcg ccagctctcc caggccctgg
 541 acacatccaa cgtgatggtg aagaagcagg tgtttgagct actggctgcc ctgtgcatct
 601 actctcccga gggccacgtg ctgaccctgg acgccctgga ccactacaag acggtgtgca
 661 gccagcagta ccgcttcagc attgtcatga acXagctcXc cggcagcgac aacgtgccct
 721 acgtggtcac cctgcXtagc gtgatcaacg ccgtcatctt gggccccgag gacctgcgcg
 781 cgcXcaccca gctgXXgaac Xagtttatcg ggctgcagct gctggacgtc ctggctcgcc
 841 tgcgagacct ggaggatgcc gacctgctga tccagctgga ggctttcgag gaggctaagg
 901 ccgaggacga ggaggagctg ctgcgagtct ctggcggggt cgacatgagc agccaccagg
 961 aggtctttgc ctccctgttc cacaaggtga gctgctcccc ggtgtctgcc cagctcctgt
1021 cggtgctgca gggcctcctg cacctggagc ccaccctccg ctccagccag ctgctctggg
1081 aggccctgga gagcctcgtg aaccgggccg tgctcctggc cagcgatgcc caggaatgca
1141 ccctggagga gtggttgag cggctcctgt ctgtcaaggg gcgacccaga ccgagccccc
1201 tggtcaaggc ccataaaagc gtccaggcca acctagacca gagccagagg ggcagctccc
1261 cgcaaaacac tacaaccccc aagcccagcg tggagggcca gcagccagca gcagctgctg
1321 cctgcgagcc cgtggaccac gccagagtg agagcatcct gaaagtttcg cagcccagag
1381 ccctggagca gcaggcgtcc accccacccc cacccccacc cccacccctg ctccctggtt
1441 ccagtgccga gccccctccc cctccccac caccccccct gccagtgtg ggggctaagg
1501 ccctcccaac agcaccccg ccccaccc tgccaggcct gggggccatg gcccccccag
1561 cacctcctct accaccaccc ctgccaggct cctgtgagtt cctgccccca ccacctccac
1621 cactcccggg cttgggatgc ccgccccac ccccacccct gctgcctggt atgggctggg
1681 gccctcctcc accccacct ccactactgc cctgcacctg cagcccccc gtggcggag
1741 gcatggagga ggtcatcgtg gcccaggtgg accatggctt gggctcagca tgggtcccca
1801 gccatcggcg ggtgaaccca cccacactgc gcatgaagaa gctgaactgg cagaagctgc
1861 catccaacgt ggcacgtgag cacaactcta tgtgggcgtc cctgagcagc ccgacgccg
1921 aggctgtgga gccgacttc tccagcatcg agcgactatt ctccttccct gcagccaagc
1981 ccaaggagcc caccatggtg gcccccggg caggaagga gccaaggag atcactttcc
2041 tcgatgccaa gaagagcctg aacctcaaca tcttcctgaa gcaatttaag tgctccaacg
2101 aggaggtcgc tgctatgatc cgggctggag ataccaccaa gtttgatgtg gaggttctca
2161 aacaactcct taagctcctt cccgagaagc acgagattga aaacctgcgg gcattcacag
2221 aggagcgagc caagctggcc agcgccgacc acttctacct cctcctgctg gccattccct
2281 gctaccagct gcgaatcgag tgcatgctgc tgtgtgaggg cgcggccgcc gtgctggaca
2341 tggtgcggcc caaggcccag ctggtgctgg ctgcctgcga aagcctgctc accagccgcc
2401 agctgcccat cttctgccag ctgatcctga gaattgggaa cttcctcaac tacggcagcc
2461 acaccggtga cgccgacggc ttcaagatca gcacattgct gaagctcacg gagaccaagt
2521 cccagcagaa ccgcgtgacg ctgctgcacc acgtgctgga ggaagcggaa aagagccacc
```

FIG. 7A

```
2581 ccgacctcct gcagctgccc cgggacctgg aacagccctc gcaagcagca gggatcaacc
2641 tggagatcat ccgctcagag gccagctcca acctgaagaa gcttctggag accgagcgga
2701 aggtgtctgc ctccgtggcc gaggtccagg agcagtacac cgagcgcctc caggccagca
2761 tctcggcctt ccgggcactg gatgagctgt ttgaggccat cgagcagaag caacgggagc
2821 tggccgacta cctgtgtgag gacgcccagc agctgtccct ggaggacacg ttcagcacca
2881 tgaaggcttt ccgggacctt ttcctccgcg ccctgaagga gaacaaggac cggaaggagc
2941 aggcggcgaa ggcagagagg aggaagcagc agctggcgga ggaggaggcg cggcggcctc
3001 ggggagagga cgggaagcct gtcaggaagg ggcccgggaa gcaggaggag gtgtgtgtca
3061 tcgatgccct gctggctgac atcaggaagg gcttccagct gcggaagaca gcccggggcc
3121 gcggggacac cgacggggcc agcaaggcag cctccatgga tcccccaaga gccacagagc
3181 ctgtggccac cagtaaccct gcaggagatc ccgtgggcag cacgcgctgt cccgcctctg
3241 agcccggcct tgatgctaca acagccagcg agtcccgggg ctgggacctt gtagacgccg
3301 tgacccccgg ccctcagccc accctggagc agttggagga gggtggtcca cggcccctgg
3361 agaggcgttc ttcctggtat gtggatgcca gcgatgtcct aaccactgag gatcccagt
3421 gccccagcc cttggagggg gcctggccgg tgactctggg agatgctcag gccctgaagc
3481 ccctcaagtt ctccagcaac cagcccctg cagccggaag ttcaaggcaa gatgccaagg
3541 atcccacgtc cttgctgggc gtcctccagg ccgaggccga cagcacaagt gaggggctgg
3601 aggacgctgt ccacagccgt ggtgccagac ccctgcagc aggcccaggt ggggatgagg
3661 acgaggacga ggaggacacg gccccagagt ccgcactgga cacatccctg acaagtcct
3721 tctccgagga tgcggtgacc gactcctcgg ggtcgggcac actccccagg gcccggggcc
3781 gggcctcaaa ggggaccggg aagcgaagga agaagcgtcc ctccaggagc aggaagagg
3841 ttcccctga ttctgatgat aataaaacaa agaaactgtg tgtgatccag taaggcctca
3901 ggcccaggcc caaggccaag tgagagagcc caggccacag gacatgctgc cattctgcca
3961 agagaggctc ttctgggggc caggctggga ctgggccccg gaaaccaaaa ctccgtgcct
4021 taccagccg gggccctcct ggagccttct tggggtgttg tggctgggaa cccgacaggc
4081 accagtgccc tgccaggcct ggtgccctcc tggaccgcct gcacgtgcca gcctcccacc
4141 tgcttcctaa aggcaaccct ggcccacacc cgcatgcgcc cggtgcagcc tgccaagggc
4201 cagtcggggg gtgctgcgtc ctgccagtgt ccaccacagc tctgcctgcc cttcagccca
4261 gcaaggttta atcaaaatgc aatgctttgc aagtctttac tgcttggagg tggctgagtt
4321 gggggccctg gcaggggta agctggcagg cagtgccatg gcaggccagg gtcccctccc
4381 atggggtctg gccccgttc cagcatgtcc agcccctgaa gttggagtgg gggcggtct
4441 gcctttgctg ccactgccag gcctctgccc tgcagctgaa acttggccat cacatcaaca
4501 gaaacccct cccagtgcca gctgcccagc gtgggcaggc cctgggaca atacaggtcc
4561 acctgagggg ctgcaggtg acacccagca gccgctgccc cctcactgcc cacccagcga
4621 gggcagccta cccgagcctg ccccctgcca ggtgtgtgcc ctgaggctgg cggctggatg
4681 cgtggccaat aaaaagcaga cctagcccgg aaaaaaaaaa aaaaa   (SEQ ID NO:21)
```

FIG. 7B

METHODS FOR DIAGNOSING AND ASSESSING RISK OF DEVELOPING GLOMERULOSCLEROSIS

CLAIM OF PRIORITY

This application is a continuation of U.S. patent application Ser. No. 15/297,804, filed Oct. 19, 2016, which is a continuation of U.S. patent application Ser. No. 13/513,447, filed Jan. 7, 2013, now U.S. Pat. No. 9,499,867, which is a 371 of International Application No. PCT/US2010/059316, filed Dec. 7, 2010, and claims priority under 35 USC § 119(e) to U.S. Patent Application Ser. No. 61/267,313, filed on Dec. 7, 2009, the entire contents of which are hereby incorporated by reference.

STATEMENT OF FEDERALLY SPONSORED RESEARCH

This invention was made with government support under Grant No. DK054931 awarded by the National Institutes of Health. The government has certain rights in the invention.

TECHNICAL FIELD

This document features method related to genetic markers of susceptibility to focal segmental glomerulosclerosis (FSGS). For example, this document provides methods of using such genetic markers for risk assessment and for diagnosing FSGS.

BACKGROUND

Many diseases affect kidney function by attacking the glomeruli, the tiny clusters of capillaries within the kidney that filter blood and remove fluid and waste products from the body in the form of urine. Diseases affecting the glomeruli include conditions with a variety of genetic and environmental causes that broadly fall within two classes: glomerulonephritis and glomerulosclerosis. Glomerulonephritis refers to inflammation of the membrane tissue in the kidney that serves as a filter, separating wastes and extra fluid from the blood. Glomerulosclerosis refers to the scarring or hardening of the glomeruli. Such scarring is typically caused by the activation of podocytes by growth factors produced by the podocytes themselves or brought to the glomerulus by circulating blood. Glomerulosclerosis may present as focal segmental glomerulosclerosis, diffuse glomerulosclerosis, nodular glomerulosclerosis, or intercapillary glomerulosclerosis. Subjects with focal segmental glomerulosclerosis (FSGS) exhibit scarring in scattered regions of the kidney that is typically limited to one part of the glomerulus and to a minority of glomeruli in the affected region. FSGS may result from a systemic disorder such as hypertension or obesity, or it may develop as an idiopathic disease. There are various subtypes of FSGS, including~primary (idiopathic or sporadic), secondary, familial, and FSGS associated with congenital syndromes.

Diagnosis of FSGS is typically based on histopathologic findings following renal biopsy, although the glomerular pathology may result from multiple different molecular or cellular processes and be unrelated to a particular disease. A characteristic feature of FSGS is proteinuria, a condition in which urine contains an abnormal amount of protein, which suggests that FSGS involves a loss or reduction of the filtration barrier between the glomerular filter and the urinary space. Since the pathophysiology of FSGS is poorly understood, the disease remains difficult to treat. In the absence of a "universal" treatment regimen for FSGS, many subjects progress to end-stage renal disease (ESRD) within 5 to 20 years. Subjects with particularly aggressive FSGS may reach ESRD within 2 to 3 years of diagnosis.

Due to the severity of symptoms associated with FSGS and the potential to progress to end-stage renal disease, there remains a need to more conclusively identify individuals at risk for developing kidney diseases and to select and optimize appropriate therapies based on an individual's genotypic subtype.

SUMMARY

Described herein are variants of the inverted formin 2 (INF2) gene, which encodes a protein involved in regulating actin polymerization and depolymerization in podocytes. As described herein, mutations in this gene are associated with glomerular diseases. These variants can be used in methods of diagnosing or determining risk of kidney disease, e.g., focal segmental glomerulosclerosis (FSGS), based on the presence of mutations that alter the level or function of INF2. For example, this document provides methods by which clinicians and other professionals can detect variants such as single nucleotide polymorphisms (SNPs) at the chromosome 14q32 locus described herein that are associated with FSGS and use such information for risk assessment and diagnosis.

In one aspect, the invention provides methods for identifying an individual at risk for developing focal segmental glomerulosclerosis (FSGS). The methods include determining a nucleic acid sequence of all or a portion of a coding sequence of INF2 in a sample from an individual; wherein the presence of a mutation in the INF2 coding sequence (e.g., a mutation that causes a change in the amino acid sequence) is indicative of an individual at risk for developing focal segmental glomerulosclerosis (FSGS).

In another aspect, the invention provides methods for diagnosing focal segmental glomerulosclerosis (FSGS). The methods include determining a nucleic acid sequence of all or a portion of a coding sequence of INF2 in a sample from an individual; wherein the presence of a mutation in the INF2 coding sequence is indicative of an individual having focal segmental glomerulosclerosis (FSGS).

In another aspect, the invention provides methods for identifying an individual at risk for developing focal segmental glomerulosclerosis (FSGS). The methods include determining a nucleic acid sequence of all or a portion of a coding sequence of INF2 in a test sample for the presence of a mutation in INF2 in:
  (i) at least one codon selected from the group consisting of codons 42, 184, 186, 198, 214, 218, and 220 (numbered relative to the coding sequence, such that codon 1 is the ATG or start codon and the codon number is the same as the number of the amino acid it encodes in SEQ ID NO:20), or
  (ii) at least one nucleotide selected from the group consisting of nucleotides 736, 795, 784, 699, 693, 796, 801, and 268 of SEQ ID NO:21;

wherein the presence of the mutation in the INF2 coding sequence is indicative of an individual at risk for developing focal segmental glomerulosclerosis (FSGS).

In another aspect, the invention provides methods for diagnosing focal segmental glomerulosclerosis (FSGS) in an individual, comprising determining a nucleic acid sequence of all or a portion of a coding sequence of INF2 in a test sample for the presence of a mutation in INF2 in (i) at least one codon selected from the group consisting of codons 42, 184, 186, 198, 214, 218, and 220, or
(ii) at least one nucleotide selected from the group consisting of nucleotides 736, 795, 784, 699, 693, 796, 801, and 268 of SEQ ID NO:21;
wherein the presence of the mutation in the INF2 coding sequence is indicative of focal segmental glomerulosclerosis (FSGS).

In some embodiments, determining a nucleic acid sequence comprises amplification of one or more exons (e.g., exons 2 or 4) or all or part of a coding sequence of INF2.

In some embodiments, the presence of a mutation in INF2 is detected by direct mutation analysis by restriction digestion. In some embodiments, the presence of a mutation in INF2 is detected by hybridization of a mutant INF2 nucleic acid probe to the INF2 gene in the test sample. In some embodiments, the mutant INF2 nucleic acid probe is fixed to a solid support. In some embodiments, detecting the presence of a mutation comprises performing microarray analysis.

In some embodiments, the presence of a mutation in INF2 sequence is detected by sequence analysis of one or more exons (e.g., exons 2 or 4) or all or part of a coding region of INF2 genomic sequence.

In some embodiments, the presence of a mutation in INF2 sequence is detected by an amplification assay (e.g., a PCR based amplification assay such as a TAQMAN®) amplification assay) of one or more exons or coding regions of INF2 genomic sequence.

In some embodiments, the presence of a mutation in INF2 is detected by hybridization of an allele-specific oligonucleotide with INF2 in the sample.

In some embodiments, the presence of a mutation in INF2 is detected by multiplex ligation dependent probe amplification assay (MLPA).

In some embodiments, the presence of a mutation in INF2 is detected by physical analysis of the nucleic acid by one or more of single strand conformation polymorphism, temperature gradient gel electrophoresis, or high performance liquid chromatography.

In some embodiments, the mutation in INF2 comprises a missense mutation in the INF2 coding sequence.

In some embodiments, the mutation results in a nonconservative amino acid substitution in the resulting protein sequence.

In some embodiments, the mutation changes an amino acid in the diaphanous inhibitory domain (DID) of INF2 (e.g., about amino acids 1-258).

In some embodiments, the mutation is in exon 2 or exon 4 of INF2.

In some embodiments, the presence of the mutation in INF2 indicates autosomal dominant focal segmental glomerulosclerosis (FSGS).

In some embodiments, the mutation in INF2 decreases INF2 levels or activity, and/or causes kidney disease in the subject, e.g., autosomal dominant focal segmental glomerulosclerosis (FSGS).

In another aspect, the invention provides methods for identifying an individual at risk for developing focal segmental glomerulosclerosis (FSGS). The methods include determining a protein sequence of all or a portion of INF2 in a sample from an individual; wherein the presence of a mutation in the INF2 protein sequence is indicative of an individual at risk for developing focal segmental glomerulosclerosis (FSGS).

In another aspect, the invention provides methods for diagnosing focal segmental glomerulosclerosis (FSGS) in an individual. The methods include determining a protein sequence of all or a portion of a protein sequence of INF2 in a sample from an individual; wherein the presence of a mutation in the INF2 protein sequence is indicative of an individual having focal segmental glomerulosclerosis (FSGS).

In another aspect, the invention provides methods for identifying an individual at risk for developing focal segmental glomerulosclerosis (FSGS). The methods include determining a protein sequence of all or a portion of the protein sequence of INF2 in a test sample for the presence of a mutation in INF2 in at least one amino acid selected from the group consisting of: L198, R214, S186, E184, R218, E220, and L42, wherein the presence of the mutation in the INF2 protein sequence is indicative of an individual at risk for developing focal segmental glomerulosclerosis (FSGS).

In another aspect, the invention provides methods for diagnosing focal segmental glomerulosclerosis (FSGS) in an individual. The methods include determining a protein sequence of all or a portion of the protein sequence of INF2 in a test sample for the presence of a mutation in INF2 in at least one amino acid selected from the group consisting of: L198, R214, S186, E184, R218, E220, and L42; wherein the presence of the mutation in the INF2 protein sequence is indicative of focal segmental glomerulosclerosis (FSGS).

In some embodiments, determining the protein sequence comprises using mass spectrometry analysis.

In some embodiments, determining the protein sequence comprises capture of INF2 protein in a sample.

In a further aspect, this document features a method of diagnosing focal segmental glomerulosclerosis (FSGS) in a human subject. The method can comprise determining a nucleic acid sequence of an INF2 gene in a sample from the human subject; determining an expected amino acid translation of the determined sequence; and comparing the expected amino acid translation with a reference amino acid sequence, wherein the reference amino acid sequence is associated with FSGS, and wherein presence of at least one amino acid variant relative to the reference amino acid sequence is indicative of a diagnosis of FSGS or an increased risk of developing FSGS in the human subject. Determining a sequence of an INF2 gene can comprise obtaining a sample comprising DNA from the human subject, and determining the sequence at an INF2 locus. The at least one amino acid variant can comprise a non-conservative amino acid substitution. The at least one amino acid variant can comprise in a non-conservative substitution in an amino acid sequence listed in Table 1. The reference amino acid sequence can be SEQ ID NO:11. The method can further comprise determining whether the amino acid variant affects expression or activity of the INF2 protein, wherein the presence of a variant that decreases INF2 expression or activity indicates that the subject has or has an increased risk of developing FSGS.

In another aspect, this document features a method for determining risk of developing FSGS in a human subject. The method can comprise detecting the presence or absence of a variant listed in Table 1 in the subject, wherein the presence of a variant associated with increased risk of FSGS indicates the subject is susceptible to FSGS. The method can further comprise selecting a treatment for the subject based on the presence or absence of a variant that correlates with susceptibility to FSGS. The method can further comprise administering the selected treatment to the human subject.

The treatment can comprise administration of an angiotensin-converting enzyme (ACE) inhibitor, a corticosteroid medicament, an immunosuppressive agent, or an alkylating agent, or any combination thereof. The ACE inhibitor can be lisinopril. The corticosteroid medicament can be selected from the group consisting of prednisone, cortisone, and hydrocortisone. The immunosuppressive agent can be selected from the group consisting of cyclosporine, tacrolimus, mycophenolate mofetil, azathioprine, and mycophenolic acid. The alkylating agent can be cyclophosphamide.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

SEQUENCE LISTING

The instant application contains a Sequence Listing that has been submitted electronically in ASCII format and is hereby incorporated by reference in its entirety. Said ASCII copy, created on Mar. 5, 2021, is named SL.txt and is 52 KB in size.

DESCRIPTION OF THE DRAWINGS

FIGS. 2A-E depict INF2 mutations (2A, 2B) and a model of mouse INF2 amino acids 1-326 which is based on the structure of mDia1 (2C, 2D, 2E). FIG. 2A shows an alignment of disease-segregating INF2 mutations and wild-type INF2 protein sequence from humans, chimpanzee, mouse, rat, opossum, and zebrafish. All of these disease mutations occur in evolutionarily conserved residues within the DID. FIG. 2B is a schematic showing INF2 protein domain structure and location of mutations. FIG. 2C shows a view of mDia1 showing the positions of A13 and R218 (medium grey). Mutated residues are shown in medium grey. Residues important for the interaction with DAD are shown in dark grey, including R106 (corresponding to K213 in mDia1), N110 (corresponding to N217 in mDia1), A149 (corresponding to A256 in mDia1), and I152 (corresponding to I259 in mDia1). Based on the crystal structure of the mDia1 DID/DAD complex (Nezami et al., Structure. 2006; 14:257-263), the alpha helical DAD is predicted to lie in the pocket containing these residues, with its N-terminus (D974) contacting R106 and N110, and L986 contacting A149 and I152. In this model, it is predicted that R218 would contact residues C-terminal to L986. FIG. 2D shows an enhanced portion of the INF2 region predicted to interact with the DAD. FIG. 2E shows a 180 degree rotation of the structure shown in FIG. 2C, showing L42, S186, and E220.

FIGS. 3A and 3B present data for a 21-year old affected member of family FSB with an E220K INF2 mutation. The subject had an estimated GFR of 96 ml/min/1.73 $m^2$ at the time of biopsy. She had 3+ urine protein and no hematuria. She developed ESRD seven years after the biopsy was performed. FIG. 3A is a light micrograph showing focal global and segmental glomerulosclerosis. PAS 100×. FIG. 3B is an electron micrograph showing segmental foot process effacement in some loops (arrowheads) and focally irregular morphology of preserved foot processes. Magnification: 4000×. The inset is a higher magnification electron micrograph showing foot processes en face, projecting from a major process. The foot processes appear irregular and jagged, often with prominent longitudinal actin bundles. 5000×. FIG. 3C presents kidney biopsy findings from a different INF2 mutant subject with an R218Q mutation, from family FGJN. This subject was 26 years old at the time of biopsy. Estimated GFR was 46 ml/min/1.73 $m^2$ and urine showed 3+ protein and trace blood at the time. FIG. 3C is a light micrograph showing focal and segmental glomerulosclerosis, with moderate chronic parenchymal damage. PAS 100×.

FIGS. 4A and 4B shows the results of RNA in situ hybridization in adult human kidney with digoxigenin-labeled probe targeted against INF2 mRNA, followed by immunohistochemical staining with labeled antibody to digoxigenin. INF2 mRNA expression was apparent in podocytes as well as some tubule cells (FIG. 4B). Magnification: 300×.

FIG. 5 is a listing of part of the coding sequence of INF2, showing the places where the variants listed in Table 1 are located.

FIG. 6 shows the sequence of INF2, with residues mutated shown as X; in some embodiments, a variant INF2 protein as described herein includes a non-wild-type amino acid in at least one of the indicated positions.

FIGS. 7A-B show the nucleotide sequence of human INF2, transcript variant 1, mRNA. Accession No. NM_022489.3. Exons are as follows:

Figure 1A:
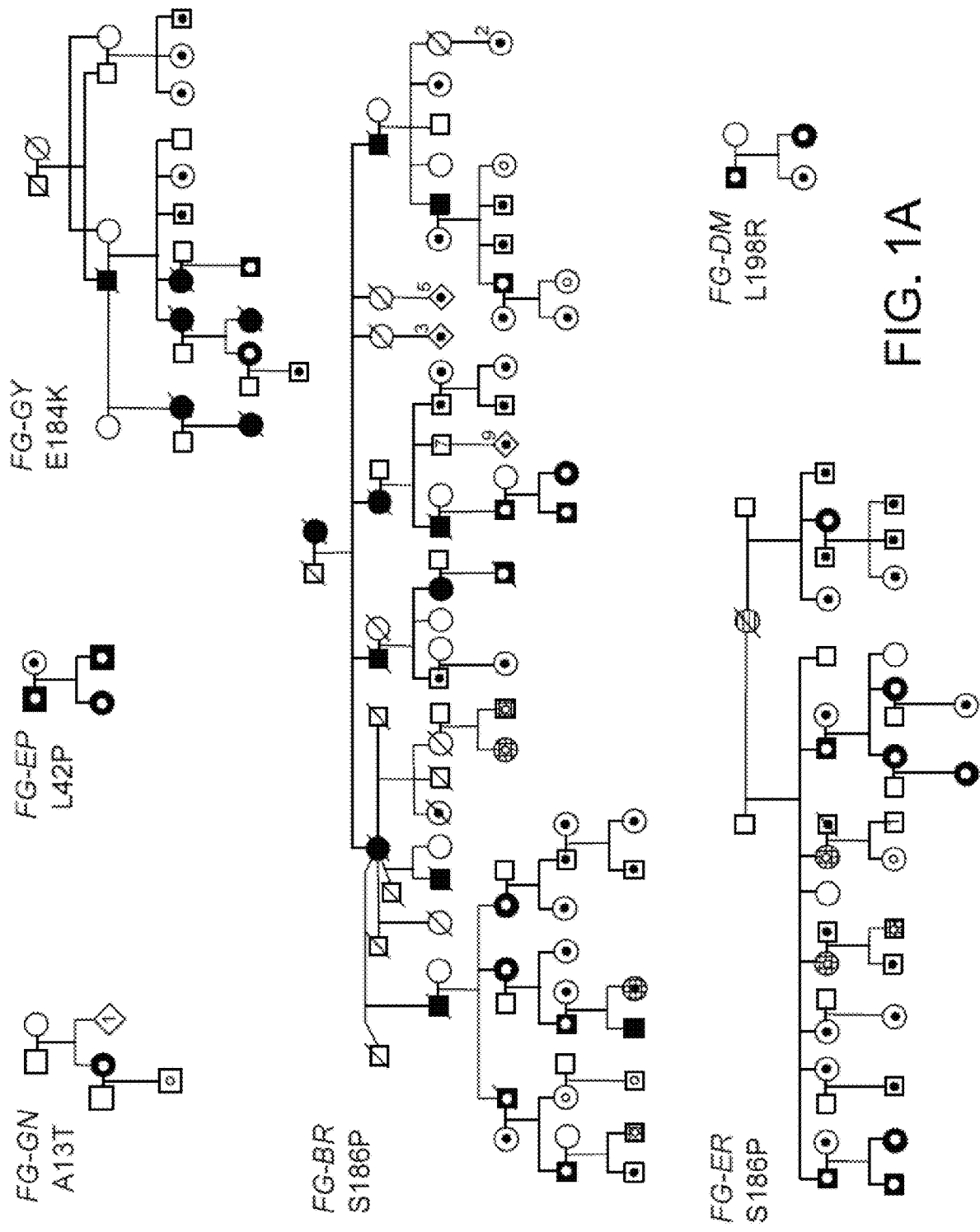
FIGS. 1A-B are pedigree identifiers for families with INF2 mutations and the specific mutations segregating in each family.

| Exon number | start nt | end nt |
| --- | --- | --- |
| 1 | 1 | 134 |
| 2 | 135 | 534 |
| 3 | 535 | 650 |
| 4 | 651 | 810 |
| 5a | 811 | 844 |
| 6 | 845 | 986 |
| 7 | 987 | 1128 |
| 8 | 1129 | 1878 |
| 9 | 1879 | 2030 |
| 10 | 2031 | 2092 |
| 11 | 2093 | 2195 |
| 12 | 2196 | 2281 |
| 13 | 2282 | 2382 |
| 14 | 2383 | 2453 |
| 15 | 2454 | 2561 |
| 16 | 2562 | 2632 |
| 17 | 2633 | 2753 |
| 18 | 2754 | 2918 |
| 19 | 2919 | 3021 |
| 20 | 3022 | 3183 |
| 21 | 3184 | 3837 |

-continued

| Exon number | start nt | end nt |
|---|---|---|
| 22 | 3838 | 3894 |
| 23 | 3895 | 4710 |

The coding region is nts 144 to 3893. Mutated nucleotides, shown as X:

| Mutated NT | Wild Type NT | Variant NT | AA Variant |
|---|---|---|---|
| 736 | t | g | L198R |
| 795 | c | t | R218W |
| 784 | g | a | R214H |
| 699 | t | c | S186P |
| 693 | g | a | E184K |
| 796 | g | a | R218Q |
| 801 | g | a | E220K |
| 268 | t | c | L42P |

DETAILED DESCRIPTION

The present invention is based at least in part on the discovery of DNA variants at the chromosome 14q32 locus that are associated with focal segmental glomerulosclerosis (FSGS) by altering the function of the INF2 protein. For example, sequence variants of INF2 segregate with the autosomal dominant form of FSGS. Without wishing to be bound by theory, it is believed that some or all of these mutations are disease-causing. Expression of INF2 mutants in cultured human podocytes alters INF2 and F-actin localization. These results suggest a novel biological pathway of regulating actin polymerization and podocyte function. Based at least in part on these discoveries are methods for assessing genetic risk based on evaluation of the nucleotide and amino acid sequences of INF2.

Definitions

As used herein, an "allele" is one of a pair or series of genetic variants at a specific genomic location. A "risk allele" is an allele that is associated with increased risk of developing a disease. Where a SNP is biallelic, one allele (the "risk allele") will be associated with increased risk, while the other allele is associated with average or decreased risk, or some variation thereof.

As used herein, "genotype" refers to the diploid combination of alleles for a given genetic polymorphism. A homozygous subject carries two copies of the same allele and a heterozygous subject carries two different alleles.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "reference sequence" refers to a sequence that is present in a subject considered to be a reference or control subject. The reference sequence as used herein is a sequence that is present in the majority of a population, i.e., the "wild-type" sequence. In some embodiments, the reference sequence is nucleic acid (e.g., genomic DNA or mRNA/cDNA) or amino acid. In some embodiments, the reference sequence of INF2 is in Genbank Accession No. NM_001031714.3 (isoform 2: nucleic acid) or NP_001026884.3 (isoform 2: amino acid). In some embodiments, the reference sequence of INF2 is in Genbank Accession No. NM_022489.3 (isoform 1: nucleic acid) or NP_071934.3 (isoform 1; amino acid). In some embodiments, the reference sequence of INF2 is in Genbank Accession No. NM_032714.1 (isoform 3; nucleic acid) or NP_116103.1 (isoform 3; amino acid). In some embodiments, the reference sequence of INF2 is nt 105155942 to 105185946 of Genbank Accession No. NC_000014.8 (genomic, GRCh37 primary reference assembly) or nt 86155942 to 86185946 of NT_026437.12 (chromosome 14 genomic contig, GRCh37 reference primary assembly). In some embodiments, the reference sequence is SEQ ID NO:9, 10, or 11.

The term "probe" refers to an oligonucleotide. In some embodiments, a probe is single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and non-isotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). In some embodiments, a probe described herein is bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. In some embodiments, targets for hybridization are derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences are performed using methods known in the art, e.g., as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30% (e.g., at least 30%, 40%, 50%, 60%, 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the comparison of sequences and determination of percent identity between two sequences is accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80% (e.g., 85%, 90%, 95%, 97% or more) identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

Methods of Diagnosing and Evaluating Risk of Developing FSGS

Described herein are methods for the diagnosis or determination of susceptibility to a glomerular disease (e.g., FSGS). "Susceptibility" does not necessarily mean that the subject will develop FSGS, but rather that the subject is, in a statistical sense, more likely to develop FSGS than an average member of the population (i.e., has an increased risk of developing FSGS). In some embodiments, the methods described herein are used to identify a subject at risk of developing FSGS. As used herein, susceptibility to FSGS exists if the subject has a variant INF2 associated with an increased risk of FSGS. Ascertaining whether the subject has a mutation in an INF2 gene, for example, is included in the concept of diagnosing or determining an increased risk of developing FSGS as used herein. Such determination is useful, for example, for purposes of diagnosis, treatment selection, and genetic counseling.

As used herein, "detecting a variant INF2" includes obtaining information regarding the identity (i.e., of a specific nucleotide), presence or absence of one or more specific sequences or alleles in a subject. Detecting a variant INF2 can, but need not, include obtaining a sample comprising DNA from a subject, and/or assessing the identity, presence or absence of a specific sequence or one or more genetic markers in the sample. The individual or organization who detects the variant INF2 need not actually carry out the physical analysis of a sample from a subject; the methods can include using information obtained by analysis of the sample by a third party. Thus the methods can include steps that occur at more than one site. In some embodiments, a sample is obtained from a subject at a first site, such as at a health care provider, or at the subject's home in the case of a self-testing kit. In some embodiments, the sample is analyzed at the same or a second site, e.g., at a laboratory or other testing facility.

Detecting a variant INF2 can also include or consist of reviewing a subject's medical history, where the medical history includes information regarding the identity, presence or absence of a sequence or an allele in the subject, e.g., the results of a genetic test.

In some embodiments, to detect a variant INF2, a biological sample that includes nucleated cells (such as blood, a cheek swab or mouthwash) is prepared and analyzed for sequence or the presence or absence of pre-selected markers. Such diagnoses may be performed by diagnostic laboratories, or, alternatively, in some embodiments, diagnostic kits are manufactured and sold to health care providers or to private individuals for self-diagnosis. In some embodiments, diagnostic or prognostic tests are performed as described herein or using well known techniques, such as described in U.S. Pat. No. 5,800,998.

In some embodiments, results of these tests, and optionally interpretive information, are returned to the subject, the health care provider or to a third party payor. The results can be used in a number of ways. In some embodiments, the information is communicated to the tested subject, e.g., with a prognosis and optionally interpretive materials that help the subject understand the test results and prognosis. In some embodiments, the information is used, e.g., by a health care provider, to determine whether to administer a treatment for FSGS, or whether a subject should be assigned to a specific category, e.g., a category associated with a specific disease, or with drug response or non-response. In some embodiments, the information is used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for FSGS if the subject has FSGS or has an increased risk of developing FSGS. The presence or absence of the allele or genotype in a subject may be ascertained by using any of the methods described herein.

INF2 Variants Associated with FSGS

This document provides methods for diagnosing or assessing risk of developing kidney disease, e.g., FSGS, based on detection or evaluation of variants in the INF2 gene.

In some embodiments, a diagnosis or determination of risk of developing FSGS is made by detecting the presence of one or more mutations, e.g., a missense mutation, e.g., a non-conservative mutation in a INF2 gene relative to a wild-type IFN2 gene. In some embodiments, the methods described herein include determining the sequence of all or part of the INF2 locus described herein as being of interest.

In some embodiments, a variant INF2 in a subject is identified based on a comparison of the sequence in the subject of the INF2 gene with a reference sequence for the same gene. For example, in some embodiments, mRNA or genomic DNA is obtained from the subject, and the sequence of all or part of the gene or transcript can be determined using methods known in the art.

As one example, INF2 variants can be identified by sequencing either genomic DNA, mRNA, or cDNA in the region in which it is desired to find a variant. For example, in some embodiments, the methods described herein include determining the sequence of the entire region of the INF2 locus described herein as being of interest, or a portion thereof (e.g., a portion of the INF2 gene or coding region that includes one or more of the mutations described herein, e.g., all or part of exons 2 and/or 4). According to one approach, primers are designed to amplify such a region, and DNA from a subject is obtained and amplified. The DNA is sequenced, and the sequence (referred to as a "subject sequence" or "test sequence") is compared with a reference sequence, which can represent the "normal" or "wild type" sequence. In some embodiments, a reference sequence is from, for example, the human draft genome sequence, publicly available in various databases, or a sequence deposited in a database such as GenBank. In some embodiments, the reference sequence is a composite of ethnically identified individuals, e.g., individuals sharing the same ethnic heritage; alternatively, the reference sequence may be a composite of individuals of diverse ethnic backgrounds. In some embodiments, a reference sequence is all or part of SEQ ID NO:9 or 10. In general, if sequencing reveals a difference between the sequenced region and the reference sequence, a variant INF2 has been identified.

In some embodiments, the methods include sequencing all or a part of the INF2 gene including all or a part of the following (partial DNA sequence of INF2 gene—portion of NM_001031714.3):

(SEQ ID NO: 9)
ATGTCGGTGAAGGAGGGCGCACAGCGCAAGTGGGCAGCGCTGAAGGAGA

AGCTGGGGCCACAGGATTCGGACCCCACGGAGGCCAACCTGGAGAGCGC

GGACCCCGAGCTGTGCATCCGGCTGCTCCAGATGCCCTCTGTGGTCAAC

TACTCCGGCCTGCGCAAGCGCCTGGAGGGCAGCGACGGCGGCTGGATGG

TGCAGTTCCTGGAGCAGAGCGGCCTGGACCTGCTGCTGGAGGCGCTGGC

GCGGCTGTCGGGCCGCGGCGTTGCACGTATCTCCGACGCCCTGCTGCAG

CTCACCTGCGTCAGCTGCGTGCGCGCCGTCATGAACTCGCGGCAGGGCA

TCGAGTACATCCTCAGCAACCAGGGCTACGTGCGCCAGCTCTCCCAGGC

CCTGGACACATCCAACGTGATGGTGAAGAAGCAGGTGTTTGAGCTACTG

GCTGCCCTGTGCATCTACTCTCCCGAGGGCCACGTGCTGACCCTGGACG

CCCTGGACCACTACAAGACGGTGTGCAGCCAGCAGTACCGCTTCAGCAT

TGTCATGAACGAGCTCTCCGGCAGCGACAACGTGCCCTACGTGGTCACC

CTGCTTAGCGTGATCAACGCCGTCATCTTGGGCCCCGAGGACCTGCGCG

CGCGCACCCAGCTGCGGAACGAGTTTATCGGGCTGCAGCTGCTGGACGT

CCTGGCTCGCCTGCGAGACCTGGAGGATGCCGACCTGCTGATCCAGCTG

GAGGCTTTCGAGGAGGCTAAGGCCGAGGACGAGGAGGAGCTGCTGCGAG

TCTCTGGCGGGGTCGACATGAGCAGCCA

In some embodiments, the methods include sequencing all or a part of the INF2 gene including all or a part of the following (coding DNA sequence of INF2 gene—portion of nucleotide sequence NM_001031714.3):

(SEQ ID NO: 10)
  1 cgccccgcgc ccgccaggag ccaccgtccg agccttgcgg agcgcggcag tgggcgccgg 61 ctgcccgcag ccctgaccc ggcccggac ggagcgccgg ccgcaccacc gccctctggc 121 cgttgcctca ccggctcggc aagatgtcgg tgaaggaggg cgcacagcgc aagtgggcag 181 cgctgaagga gaagctgggg ccacaggatt cggaccccac ggaggccaac ctggagagcg 241 cggaccccga gctgtgcatc cggctgctcc agatgccctc tgtggtcaac tactccggcc 301 tgcgcaagcg cctggagggc agcgacggcg gctggatggt gcagttcctg gagcagagcg -continued

```
 361 gcctggacct gctgctggag gcgctggcgc ggctgtcggg ccgcggcgtt gcacgtatct
 421 ccgacgccct gctgcagctc acctgcgtca gctgcgtgcg cgccgtcatg aactcgcggc
 481 agggcatcga gtacatcctc agcaaccagg gctacgtgcg ccagctctcc caggccctgg
 541 acacatccaa cgtgatggtg aagaagcagg tgtttgagct actggctgcc ctgtgcatct
 601 actctcccga gggccacgtg ctgaccctgg acgccctgga ccactacaag acggtgtgca
 661 gccagcagta ccgcttcagc attgtcatga cgagctctc cggcagcgac aacgtgccct
 721 acgtggtcac cctgcttagc gtgatcaacg ccgtcatctt gggccccgag gacctgcgcg
 781 cgcgcaccca gctgcggaac gagtttatcg ggctgcagct gctggacgtc ctggctcgcc
 841 tgcgagacct ggaggatgcc gacctgctga tccagctgga ggctttcgag gaggctaagg
 901 ccgaggacga ggaggagctg ctgcgagtct ctggcggggt cgacatgagc agccaccagg
 961 aggtctttgc ctccctgttc cacaaggtga gctgctcccc ggtgtctgcc cagctcctgt
1021 cggtgctgca gggcctcctg cacctggagc ccaccctccg ctccagccag ctgctctggg
1081 aggccctgga gagcctcgtg aaccgggccg tgctcctggc cagcgatgcc caggaatgca
1141 ccctggagga agtggttgag cggctcctgt ctgtcaaggg gcgacccaga ccgagccccc
1201 tggtcaaggc ccataaaagc gtccaggcca acctagacca gagccagagg ggcagctccc
1261 cgcaaaacac tacaaccccc aagcccagcg tggagggcca gcagccagca gcagctgctg
1321 cctgcgagcc cgtggaccac gcccagagtg agagcatcct gaaagtttcg cagcccagag
1381 ccctggagca gcaggcgtcc accccacccc cacccccacc cccacccctg ctccctggtt
1441 ccagtgccga gccccctccc cctcccccac caccccccct gcccagtgtg ggggctaagg
1501 ccctcccaac agcaccccg ccccacccc tgccaggcct ggggccatg gccccccag
1561 cacctcctct accaccaccc ctgccaggct cctgtgagtt cctgccccca ccacctccac
1621 cactcccggg cttgggatgc ccgcccccac ccccacccct gctgctggt atgggctggg
1681 gccctcctcc acccccacct ccactactgc cctgcacctg cagcccccc gtggcgggag
1741 gcatggagga ggtcatcgtg gcccaggtgg accatggctt gggctcagca tgggtcccca
1801 gccatcggcg ggtgaaccca cccacactgc gcatgaagaa gctgaactgg cagaagctgc
1861 catccaacgt ggcacgtgag cacaactcta tgtgggcgtc cctgagcagc cccgacgccg
1921 aggctgtgga gcccgacttc tccagcatcg agcgactatt ctccttccct gcagccaagc
1981 ccaaggagcc caccatggtg gcccccgggg ccaggaagga gcccaaggag atcactttcc
2041 tcgatgccaa gaagagcctg aacctcaaca tcttcctgaa gcaatttaag tgctccaacg
2101 aggaggtcgc tgctatgatc cgggctggag ataccaccaa gtttgatgtg gaggttctca
2161 aacaactcct taagctcctt cccgagaagc acgagattga aaacctgcgg gcattcacag
2221 aggagcgagc caagctggcc agcgccgacc acttctacct cctcctgctg gccattccct
2281 gctaccagct gcgaatcgag tgcatgctgc tgtgtgaggg cgcggccgcc gtgctggaca
2341 tggtgcggcc caaggcccag ctggtgctgg ctgcctgcga aagcctgctc accagccgcc
2401 agctgcccat cttctgccag ctgatcctga gaattgggaa cttcctcaac tacggcagcc
2461 acaccggtga cgccgacggc ttcaagatca gcacattgct gaagctcacg gagaccaagt
2521 cccagcagaa ccgcgtgacg ctgctgcacc acgtgctgga ggaagcggaa aagagccacc
2581 ccgacctcct gcagctgccc cgggacctgg aacagccctc gcaagcagca gggatcaacc
2641 tggagatcat ccgctcagag gccagctcca acctgaagaa gcttctggag accgagcgga
2701 aggtgtctgc ctccgtggcc gaggtccagg agcagtacac cgagcgcctc caggccagca
```

-continued

```
2761 tctcggcctt ccgggcactg gatgagctgt ttgaggccat cgagcagaag caacgggagc 2821 tggccgacta cctgtgtgag gacgcccagc agctgtccct ggaggacacg ttcagcacca 2881 tgaaggcttt ccgggacctt ttcctccgcg ccctgaagga gaacaaggac cggaaggagc 2941 aggcggcgaa ggcagagagg aggaagcagc agctggcgga ggaggaggcg cggcggcctc 3001 ggggagagga cgggaagcct gtcaggaagg ggcccgggaa gcaggaggag gtgtgtgtca 3061 tcgatgccct gctggctgac atcaggaagg gcttccagct gcggaagaca gcccggggcc 3121 gcggggacac cgacgggggc agcaaggcag cctccatgga tcccccaaga gccacagagc 3181 ctgtggccac cagtaaccct gcaggagatc ccgtgggcag cacgcgctgt cccgcctctg 3241 agcccggcct tgatgctaca acagccagcg agtcccgggg ctgggacctt gtagacgccg 3301 tgaccccggg ccctcagccc accctggagc agttggagga gggtggtcca cggcccctgg 3361 agaggcgttc ttcctggtat gtggatgcca gcgatgtcct aaccactgag gatccccagt 3421 gcccccagcc cttggagggg gcctggccgg tgactctggg agatgctcag gccctgaagc 3481 ccctcaagtt ctccagcaac cagcccctg cagccggaag ttcaaggcaa gatgccaagg 3541 atcccacgtc cttgctgggc gtcctccagg ccgaggccga cagcacaagt gaggggctgg 3601 aggacgctgt ccacagccgt ggtgccagac ccctgcagc aggcccaggt ggggatgagg 3661 acgaggacga ggaggacacg gccccagagt ccgcactgga cacatccctg acaagtcct 3721 tctccgagga tgcggtgacc gactcctcgg ggtcgggcac actccccagg gcccggggcc 3781 gggcctcaaa ggggaccggg aagcgaagga agaagcgtcc ctccaggagc caggaaggcc 3841 tcaggcccag gcccaaggcc aagtgagaga gcccaggcca caggacatgc tgccattctg 3901 ccaagagagg ctcttctggg ggccaggctg ggactgggcc ccggaaacca aaactccgtg 3961 ccttacccag ccggggcct cctggagcct tcttggggtg ttgtggctgg gaacccgaca 4021 ggcaccagtg ccctgccagg cctggtgccc tcctggaccg cctgcacgtg ccagcctccc 4081 acctgcttcc taaaggcaac cctggcccac acccgcatgc gcccggtgca gcctgccaag 4141 ggccagtcgg ggggtgctgc gtcctgccag tgtccaccac agctctgcct gcccttcagc 4201 ccagcaaggt ttaatcaaaa tgcaatgctt tgcaagtctt tactgcttgg aggtggctga 4261 gttgggggcc ctgggcaggg gtaagctggc aggcagtgcc atggcaggcc agggtcccct 4321 cccatggggt ctggcccccg ttccagcatg tccagcccct gaagttggag tgggggcgg 4381 tctgcctttg ctgccactgc caggcctctg ccctgcagct gaaacttggc catcacatca 4441 acagaaaacc cctcccagtg ccagctgccc agcgtgggca ggccctgggg acaatacagg 4501 tccacctgag gggctgcagg gtgacaccca gcagccgctg cccctcact gcccacccag 4561 cgagggcagc ctacccgagc ctgcccctg ccaggtgtgt gccctgaggc tggcggctgg 4621 atgcgtggcc aataaaaagc agacctagcc cggaaaaaaa aaaaaaa
```

In some embodiments, the methods include detecting the presence of one or more missense mutations in a region defined by flanking SNPs rs3783397 (at approximately 103 Mb on the Marshfield map) and rs6576201 (at approximately 106 Mb).

In some embodiments, all or part of the nucleic acid sequence is "translated" into a predicted amino acid sequence based on known rules of codon-amino acid specification. This predicted amino acid sequence can be evaluated for the presence of one or more differences from the reference amino acid sequence, wherein the presence of a difference (e.g., a variant) indicates an increased risk of developing FSGS. In some embodiments, the presence of a missense mutation, e.g., a non-conservative variant, in the amino acid sequence indicates an increased risk of FSGS. In some embodiments, a variant amino acid sequence is detected directly, e.g., using methods known in the art, such as methods using antibodies that bind specifically to a variant of INF2 protein but not to wild-type, or by direct sequencing of the protein, e.g., using mass spectrometry analysis or other methods known in the art.

In some embodiments, the reference amino acid sequence includes all or a part of the following:

(SEQ ID NO: 11)
MSVKEGAQRKWAALKEKLGPQDSDPTEANLESADPELCIRLLQMPSVVN

YSGLRKRLEGSDGGWMVQFLEQSGLDLLLEALARLSGRGVARISDALLQ

LTCVSCVRAVMNSRQGIEYILSNQGYVRQLSQALDTSNVMVKKQVFELL

AALCIYSPEGHVLTLDALDHYKTVCSQQYRFSIVMNELSGSDNVPYVVT

LLSVINAVILGPEDLRARTQLRNEFIGLQLLDVLARLRDLEDADLLIQL

EAFEEAKAEDEEELLRVSGGVDMSSHQEVFASLFHKVSCSPVSAQLLSV

LQGLLHLEPTLRSSQLLWEALESLVNRAVLLASDAQECTLEEVVERLLS

VKGRPRPSPLVKAHKSVQANLDQSQRGSSPQNTTTPKPSVEGQQPAAAA

ACEPVDHAQSESILKVSQPRALEQQASTPPPPPPPPLLPGSSAEPPPPP

PPPPLPSVGAKALPTAPPPPPLPLGLGAMAPPAPPLPPPLPGSCEFLPPP

PPPLPGLGCPPPPPPLLPGMGWGPPPPPPPLLPCTCSPPVAGGMEEVIV

AQVDHGLGSAWVPSHRRVNPPTLRMKKLNWQKLPSNVAREHNSMWASLS

SPDAEAVEPDFSSIERLFSFPAAKPKEPTMVAPRARKEPKEITFLDAKK

SLNLNIFLKQFKCSNEEVAAMIRAGDTTKFDVEVLKQLLKLLPEKHEIE

-continued
NLRAFTEERAKLASADHFYLLLLAIPCYQLRIECMLLCEGAAAVLDMVR

PKAQLVLAACESLLTSRQLPIFCQLILRIGNFLNYGSHTGDADGFKIST

LLKLTETKSQQNRVTLLHHVLEEAEKSHPDLLQLPRDLEQPSQAAGINL

EIIRSEASSNLKKLLETERKVSASVAEVQEQYTERLQASISAFRALDEL

FEAIEQKQRELADYLCEDAQQLSLEDTFSTMKAFRDLFLRALKENKDRK

EQAAKAERRKQQLAEEEARRPRGEDGKPVRKGPGKQEEVCVIDALLADI

RKGFQLRKTARGRGDTDGGSKAASMDPPRATEPVATSNPAGDPVGSTRC

PASEPGLDATTASESRGWDLVDAVTPGPQPTLEQLEEGGPRPLERRSSW

YVDASDVLTTEDPQCPQPLEGAWPVTLGDAQALKPLKFSSNQPPAAGSS

RQDAKDPTSLLGVLQAEADSTSEGLEDAVHSRGARPPAAGPGGDEDEDE

EDTAPESALDTSLDKSFSEDAVTDSSGSGTLPRARGRASKGTGKRRKKR

PSRSQEGLRPRPKAK

In some embodiments, the methods further include verifying that the variant affects the activity or expression of INF2 protein, wherein variants that do not affect expression or activity of INF2 do not indicate an increased risk of FSGS, but variants that decrease activity or expression of FSGS indicate an increased risk of FSGS.

To determine whether the variant causes a decrease in activity or function of the protein, any method known in the art can be used. For example, ins some embodiments a recombinant protein is produced using known molecular biological techniques, e.g., obtaining a wild type or reference sequence (e.g., genomic or cDNA), using mutagenesis (e.g., site-directed mutagenesis) to alter the sequence to reflect the mutation, and expressing the mutated protein in a cell, e.g., a mammalian cell, and assaying for protein levels and/or activity of the protein.

In some embodiments, the presence of a variant INF2 is identified based on detection of the presence of one or more sequence variants. Tables 1 and 2 list exemplary sequence variants that are used in some embodiments of the present methods. One of skill in the art will appreciate that additional risk alleles may be identified, e.g., via TDT using families with multiple affected individuals and verified by Case/Control comparisons, e.g., using the methods and markers described herein. Using the SNP markers described herein, one can identify alleles in these genes relating to diagnosis or genetic risk of developing FSGS. These alleles can then be used to determine risk of developing FSGS. The allelic variants thus identified can be used for diagnosis and for assessing genetic risk.

TABLE 1

Alleles of INF2 Relating to Diagnosis or Risk of Developing FSGS

| SEQ ID NO: | sequence | | | | | | Risk Allele | Non-conservative Amino Acid Change |
|---|---|---|---|---|---|---|---|---|
| 1 | gtc | acc | ctg | c[t/G]t | agc | gtg | atc | G | L198R |
| 12 | V | T | L | L/R | S | V | I | | |
| 2 | acc | cag | ctg | c[c/T]gg | aac | gag | ttt | T | R218W |
| 13 | T | Q | L | R/W | N | E | F | | |
| 3 | cgc | gcg | c[g/A]c | acc | cag | | | A | R124H |
| 14 | R | A | R/H | T | Q | | | | |
| 4 | gag | ctc | [t/C]cc | ggc | agc | gac | | C | S186P |
| 15 | E | L | S/P | G | S | D | | | |

TABLE 1-continued

Alleles of INF2 Relating to Diagnosis or Risk of Developing FSGS

| SEQ ID NO: | sequence | | | | | | Risk Allele | Non-conservative Amino Acid Change |
|---|---|---|---|---|---|---|---|---|
| 5<br>16 | gtc<br>V | atg<br>M | aac<br>N | [g/A]ag<br>E/K | ctc<br>L | tcc<br>S | A | E184K |
| 6<br>17 | cag<br>Q | ctg<br>L | c[g/A]g<br>R/Q | aac<br>N | gag<br>E | ttt<br>F | A | R218Q |
| 7<br>18 | ctg<br>L | cgg<br>R | aac<br>N | [g/A]ag<br>E/K | ttt<br>F | atc<br>I | A | E220K |
| 8<br>19 | cgg<br>R | ctg<br>L | c[t/C]c<br>L/P | cag<br>Q | atg<br>M | | C | L42P |

In some embodiments, to identify INF2 variants described herein, a biological sample that includes nucleated cells (such as blood, a cheek swab, or mouthwash) is prepared and analyzed for sequence, or for the presence or absence of preselected markers. In some embodiments, direct analysis of INF2 proteins is used to detect the presence of mutations, using samples comprising INF2 proteins from the subject, e.g., tissue samples, e.g., from a tissue biopsy; in some embodiments, a kidney tissue biopsy is used. Such determinations can be performed using methods known in the art by diagnostic laboratories, or, alternatively, diagnostic kits can be manufactured and sold to health care providers or to private individuals for self-diagnosis; such kits can include primers, probes, or antibodies that bind specifically to a mutation in INF2, e.g., as described herein. Diagnostic or prognostic tests can be performed as described herein or using well known techniques, such as described in U.S. Pat. No. 5,800,998. The presence or absence of the allelic variant in a subject may be ascertained by using any of the methods described herein. In some cases, results of these tests, and optionally interpretive information, can be returned to the subject or the health care provider. Information gleaned from the methods described herein can also be used to select or stratify subjects for a clinical trial. For example, the presence of a selected allelic variant described herein can be used to select a subject for a clinical trial, e.g., a trial of a treatment or prophylactic for FSGS.

The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, the biological sample is processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., *Current Protocols in Molecular Biology*, eds., John Wiley & Sons (2003). The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAAMPR Tissue Kit (Qiagen, Chatsworth, CA) and the WIZARD® Genomic DNA purification kit (Promega).

Identifying Additional Genetic Markers of FSGS

In general, genetic markers of FSGS can be identified using any of a number of methods that are known in the art. For example, numerous variants in the regions described herein are known to exist and are available in public databases, which can be searched using methods and algorithms known in the art. The methods can thus include the analysis of other genes at the chromosome 14q32 locus relating to FSGS, e.g., ADSSL1 (adenylosuccinate synthase like 1); SIVA1 (apoptosis-inducing factor); AKT1 (RAC-alpha serine/threonine-protein kinase); PLD4 (phospholipase D4); AHNAK2 (AHNAK nucleoprotein 2); CDCA4 (cell division cycle associated 4); GPR132 (G protein-coupled receptor 132); JAG2 (jagged 2); NUDT14 (nucleoside diphosphate-linked moiety X motif 14); BRF1 (B-related factor 1); PACS2 (phosphofurin acidic cluster sorting protein 2); MTA1 (metastasis associated 1); CRIP2 (cysteine-rich intestinal protein 2); and CRIP1 (cysteine-rich intestinal protein 1).

The methods described herein can also include determining the presence or absence of other markers known or suspected to be associated with FSGS, e.g., markers outside of a region identified herein, including, for example, markers on chromosome 14 and other chromosomes, e.g., in the region of 14q32. In some cases, the methods include determining the presence or absence of one or more other markers that are or may be associated with FSGS, e.g., in one or more genes. For example, the methods can include additionally determining the presence or absence of SNPs of MYH9, a functional candidate gene expressed in kidney podocytes or actin-related protein 3 (Arp3), a gene mutated in a rat model of FSGS. See, e.g., Kopp et al., *Nat Genet.* 40(10): 1175-84 (2008); Akiyama et al., *Mamm. Genome* 19(1):41-50 (2008).

Methods of Determining the Presence of a Variant INF2

The absence or presence of a variant INF2 associated with FSGS as described herein can be determined using methods known in the art. For example, gel electrophoresis, capillary electrophoresis, size exclusion chromatography, sequencing, and/or arrays can be used to detect the presence or absence of a variant INF2. Amplification of nucleic acids, where desirable, can be accomplished using methods known in the art, e.g., PCR. In one example, a sample (e.g., a sample comprising genomic DNA), is obtained from a subject. The DNA in the sample is then examined to identify a variant INF2 as described herein. The presence of the variant INF2 can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular variant.

Other methods of nucleic acid analysis can include direct manual sequencing (Church and Gilbert, *Proc. Natl. Acad. Sci. USA* 81: 1991-1995 (1988); Sanger et al., *Proc. Natl. Acad. Sci. USA* 74:5463-5467 (1977); Beavis et al., U.S. Pat. No. 5,288,644); automated fluorescent sequencing; single-stranded conformation polymorphism assays (SSCP) (Schafer et al., *Nat. Biotechnol.* 15:33-39 (1995)); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., *Proc. Natl. Acad. Sci. USA* 86:232-236 (1989)); denaturing high performance liquid chromatography (DHPLC, Underhill et al., *Genome Res.* 7:996-1005 (1997)); infrared matrix-assisted laser desorption/ionization (IR-MALDI) mass spectrometry (WO 99/57318); mobility shift analysis (Orita et al., *Proc. Natl. Acad. Sci. USA* 86:2766-2770 (1989)); restriction enzyme analysis (Flavell et al., *Cell* 15:25 (1978); Geever et al., *Proc. Natl. Acad. Sci. USA* 78:5081 (1981)); quantitative real-time PCR (Raca et al., *Genet Test* 8(4):387-94 (2004)); heteroduplex analysis; chemical mismatch cleavage (CMC) (Cotton et al., *Proc. Natl. Acad. Sci. USA* 85:4397-4401 (1985)); RNase protection assays (Myers et al., *Science* 230:1242 (1985)); use of polypeptides that recognize nucleotide mismatches, e.g., *E. coli* mutS protein; allele-specific PCR, and combinations of such methods. See, e.g., Gerber et al., U.S. Pat. Publication No. 2004/0014095 which is incorporated herein by reference in its entirety.

Sequence analysis can also be used to detect specific polymorphic variants. For example, polymorphic variants can be detected by sequencing exons, introns, 5' untranslated sequences, or 3' untranslated sequences. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined. Real-time pyrophosphate DNA sequencing is yet another approach to detection of polymorphisms and polymorphic variants (Alderborn et al., *Genome Research* 10(8): 1249-1258 (2000)). Additional methods include, for example, PCR amplification in combination with denaturing high performance liquid chromatography (dHPLC) (Underhill et al., *Genome Research* 7(10):996-1005 (1997)).

In some embodiments, the methods described herein include determining the sequence of the entire region of the INF2 locus described herein as being of interest. For example, a method provided herein can include determining a nucleic acid sequence of an INF2 gene in a sample from a human subject, determining an expected amino acid translation of nucleic acid sequence; and comparing the expected amino acid translation with a reference amino acid sequence associated with FSGS. In such a method, the presence of at least one amino acid variant (e.g., a non-conservative amino acid substitution) relative to the reference amino acid sequence can be indicative of a diagnosis of FSGS or an increased risk of developing FSGS in the human subject. For example, a amino acid variant can comprise a non-conservative substitution such as one of the amino acid substitutions encoded by the sequences set forth as SEQ ID NOs: 1-8. In some cases, the sequence of the IFN2 locus can be determined using SNPs rs3783397 and rs6576201. In some embodiments, the sequence is determined on both strands of DNA.

In order to detect sequence variants, it may be desirable to amplify a portion of genomic DNA (gDNA) or cDNA encompassing the variant site. Such regions can be amplified and isolated by PCR using oligonucleotide primers designed based on genomic and/or cDNA sequences that flank the site. PCR refers to procedures in which target nucleic acid (e.g., genomic DNA) is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. See e.g., *PCR Primer: A Laboratory Manual*, Dieffenbach and Dveksler, (Eds.); McPherson et al., *PCR Basics: From Background to Bench* (Springer Verlag, 2000); Mattila et al., *Nucleic Acids Res.*, 19:4967 (1991); Eckert et al., *PCR Methods and Applications*, 1:17 (1991); *PCR* (eds. McPherson et al., IRL Press, Oxford); and U.S. Pat. No. 4,683,202. Other amplification methods that may be employed include the ligase chain reaction (LCR) (Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), self-sustained sequence replication (Guatelli et al., *Proc. Nat. Acad. Sci. USA* 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth, Minn.), MacVector (Kodak/IBI), and the GCG suite of sequence analysis programs (Genetics Computer Group, Madison, Wis. 53711).

In some cases, PCR conditions and primers can be developed that amplify a product only when the variant allele is present or only when the wild type allele is present (MSPCR or allele-specific PCR). For example, subject DNA and a control can be amplified separately using either a wild type primer or a primer specific for the variant allele. Each set of reactions is then examined for the presence of amplification products using standard methods to visualize the DNA. For example, the reactions can be size-separated by agarose gel electrophoresis and the DNA visualized by staining with ethidium bromide or other DNA intercalating dye. In DNA samples from heterozygous subjects, reaction products would be detected in each reaction.

Real-time quantitative PCR can also be used to determine copy number. Quantitative PCR permits both detection and quantification of specific DNA sequence in a sample as an absolute number of copies or as a relative amount when normalized to DNA input or other normalizing genes. A key feature of quantitative PCR is that the amplified DNA product is quantified in real-time as it accumulates in the reaction after each amplification cycle. Methods of quantification can include the use of fluorescent dyes that intercalate with double-stranded DNA, and modified DNA oligonucleotide probes that fluoresce when hybridized with a complementary DNA.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant conferring susceptibility to FSGS.

In some cases, allele-specific oligonucleotides can also be used to detect the presence of a variant. For example, variants can be detected by performing allele-specific hybridization or allele-specific restriction digests. Allele specific hybridization is an example of a method that can be used to detect sequence variants, including complete haplotypes of a subject (e.g., a mammal such as a human). See Stoneking et al., *Am. J. Hum. Genet.* 48:370-382 (1991); and Prince et al., *Genome Res.* 11:152-162 (2001). An "allele-specific oligonucleotide" (also referred to herein as an "allele-specific oligonucleotide probe") is an oligonucleotide that is specific for a particular polymorphism can be prepared using standard methods (see Ausubel et al., *Current Protocols in Molecular Biology*, supra). Allele-specific oligonucleotide probes typically can be approximately 10-50 base pairs, preferably approximately 15-30 base pairs, that specifically hybridize to a nucleic acid region that contains a polymorphism. Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. In some cases, dot-blot hybridization of amplified oligonucleotides with allele-specific oligonucleotide (ASO) probes can be performed. See, for example, Saiki et al., *Nature* (London) 324:163-166 (1986).

In some embodiments, allele-specific restriction digest analysis can be used to detect the existence of a variant INF2, if the variants result in the creation or elimination of a restriction site. Allele-specific restriction digests can be performed in the following manner. A sample containing genomic DNA is obtained from the individual and genomic DNA is isolated for analysis. For nucleotide sequence variants that introduce a restriction site, restriction digest with the particular restriction enzyme can differentiate the alleles. In some cases, polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a variant and is therefore indicative of the presence or absence of susceptibility to FSGS. For sequence variants that do not alter a common restriction site, mutagenic primers can be designed that introduce a restriction site when the variant allele is present or when the wild type allele is present. For example, a portion of a nucleic acid can be amplified using the mutagenic primer and a wild type primer, followed by digest with the appropriate restriction endonuclease.

In some embodiments, fluorescence polarization template-directed dye-terminator incorporation (FP-TDI) is used to determine which of multiple polymorphic variants of a polymorphism is present in a subject (Chen et al., *Genome Research* 9(5):492-498 (1999)). Rather than involving use of allele-specific probes or primers, this method employs primers that terminate adjacent to a variant site, so that extension of the primer by a single nucleotide results in incorporation of a nucleotide complementary to the polymorphic variant at the polymorphic site.

In some cases, DNA containing an amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe to DNA from the subject is indicative of susceptibility to FSGS.

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a variant other than the reference sequence. If multiple variants exist at a site, this can be appropriately indicated by specifying which ones are present in the subject. Any of the detection means described herein can be used to determine the genotype of a subject with respect to one or both copies of the variant present in the subject's genome.

Methods of nucleic acid analysis to detect variants can include, e.g., microarray analysis. Hybridization methods, such as Southern analysis, Northern analysis, or in situ hybridizations, can also be used (see Ausubel et al., *Current Protocols in Molecular Biology*, eds., John Wiley & Sons (2003)). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

In some embodiments, it is desirable to employ methods that can detect the presence of multiple variants (e.g., variants at a plurality of sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel can also be performed so as to detect the presence of multiple variants (e.g., variants at a plurality of polymorphic sites) in parallel or substantially simultaneously.

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70% (e.g., 80%, 90%, 95%, 98% or more) identity to the target sequence. The probe sequence must also be sufficiently long so that the probe exhibits selectivity for the target sequence over non-target sequences. For example, the probe will be at least 20 (e.g., 25, 30, 35, 50, 100, 200, 300, 400, 500, 600, 700, 800, 900 or more) nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as polymerase chain reaction (PCR), ligase chain reaction (LCR), etc., for amplification of a target sequence.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially such from Applied Biosystems, e.g., the Assays-on-Demand SNP kits. Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via PCR. See, for example, Nath and Johnson, *Biotechnic. Histochem.* 73(1):6-22 (1998); Wheeless et al., *Cytometry* 17:319-326 (1994); and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), TEXAS RED™ (Molecular Probes, Inc., Eugene, OR), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a, 4a diaza-3-indacenepropionic acid, eosin-5-isothiocyanate, erythrosin-5-isothiocyanate, and CASCADE™ blue acetylazide (Molecular Probes, Inc., Eugene, OR). Fluorescently labeled probes can be viewed with a fluorescence microscope and an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

In another aspect, the invention features arrays that include a substrate having a plurality of addressable areas, and methods of using them. At least one area of the plurality includes a nucleic acid probe that binds specifically to a sequence comprising a variant described herein, and can be used to detect the absence or presence of said variant, e.g., one or more SNPs, microsatellites, minisatellites, or indels, as described herein, e.g., to determine a haplotype comprising a plurality of variants. For example, the array can include one or more nucleic acid probes that can be used to detect a variant described herein. In some embodiments, the array further includes at least one area that includes a nucleic acid probe that can be used to specifically detect another marker associated with FSGS, as described herein. In some embodiments, the probes are nucleic acid capture probes.

Generally, microarray hybridization is performed by hybridizing a nucleic acid of interest (e.g., a nucleic acid encompassing a polymorphic site) with the array and detecting hybridization using nucleic acid probes. In some cases, the nucleic acid of interest is amplified prior to hybridization. Hybridization and detecting are generally carried out according to standard methods. See, e.g., Published PCT Application Nos. WO 92/10092 and WO 95/11995, and U.S. Pat. No. 5,424,186. For example, the array can be scanned to determine the position on the array to which the nucleic acid hybridizes. The hybridization data obtained from the scan is typically in the form of fluorescence intensities as a function of location on the array.

Arrays can be formed on substrates fabricated with materials such as paper, glass, plastic (e.g., polypropylene, nylon, or polystyrene), polyacrylamide, nitrocellulose, silicon, optical fiber, or any other suitable solid or semisolid support, and can be configured in a planar (e.g., glass plates, silicon chips) or three dimensional (e.g., pins, fibers, beads, particles, microtiter wells, capillaries) configuration. Methods for generating arrays are known in the art and include, e.g., photolithographic methods (see, e.g., U.S. Pat. Nos. 5,143, 854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. Oligonucleotide probes forming an array may be attached to a substrate by any number of techniques, including, without limitation, (i) in situ synthesis (e.g., high-density oligonucleotide arrays) using photolithographic techniques; (ii) spotting/printing at medium to low density on glass, nylon or nitrocellulose; (iii) by masking, and (iv) by dot-blotting on a nylon or nitrocellulose hybridization membrane. Oligonucleotides also can be non-covalently immobilized on a substrate by hybridization to anchors, by means of magnetic beads, or in a fluid phase such as in microtiter wells or capillaries.

Arrays can include multiple detection blocks (i.e., multiple groups of probes designed for detection of particular variants). Such arrays can be used to analyze multiple different variants. Detection blocks may be grouped within a single array or in multiple, separate array's so that varying conditions (e.g., conditions optimized for particular variants) may be used during the hybridization. For example, it may be desirable to provide for the detection of those variants that fall within G-C rich stretches of a genomic sequence, separately from those falling in A-T rich segments. General descriptions of using oligonucleotide arrays for detection of variants can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample (e.g., a portion of genomic DNA that includes at least a portion of human chromosome 14q32 (e.g., a region between SNPs rs3783397 and rs6576201) and/or optionally, a different portion of genomic DNA (e.g., a portion that includes a different portion of a human chromosome (e.g., including another region associated with FSGS)), and detecting binding of a nucleic acid from the sample to the array. Optionally, the method includes amplifying nucleic acid from the sample, e.g., genomic DNA that includes at least a portion of an IFN2 gene, and, optionally, a region that includes another region associated with FSGS, prior to or during contact with the array.

In some aspects, the methods described herein can include using an array that can ascertain differential expression patterns or copy numbers of one or more genes in samples from normal and affected individuals (see, e.g., Redon et al., *Nature* 444(7118): 444-54 (2006)). For example, arrays of probes to a marker described herein can be used to measure variants between DNA from a subject having FSGS and control DNA, e.g., DNA obtained from an individual that does not have FSGS, and has no risk factors for FSGS. Since the clones on the array contain sequence tags, their positions on the array are accurately known relative to the genomic sequence. Different hybridization patterns between DNA from an individual afflicted with FSGS and DNA from a normal individual at areas in the array corresponding to markers in the human chromosome 14q32 locus as described herein, and, optionally, one or more other regions associated with FSGS, are indicative of a risk of such glomerular diseases. Methods for array production, hybridization, and analysis are described, e.g., in Snijders et al., *Nat. Genet.* 29:263-264 (2001); Klein et al., *Proc. Natl Acad. Sci. USA* 96:4494-99 (1999): Albertson et al., *Breast Cancer Res. and Treatment* 78:289-298 (2003); and Snijders et al. "BAC microarray based comparative genomic hybridization," in Zhao et al. (eds), *Bacterial Artificial Chromosomes: Methods and Protocols*, Methods in Molecular Biology, Humana Press, 2002.

In another aspect, the invention features methods of determining the absence or presence of a variant associated with altered actin function in podocytes and/or risk of FSGS as described herein, using an array described above. The methods include providing a two dimensional array having a plurality of addresses, each address of the plurality being positionally distinguishable from each other address of the plurality having a unique nucleic acid capture probe. In some embodiments, the second and third samples are from first or second-degree relatives of the test subject. Binding, e.g., in the case of a nucleic acid hybridization, with a capture probe at an address of the plurality, can be detected by any method known in the art, e.g., by detection of a signal generated from a label attached to the nucleic acid.

Methods of Determining Treatment Regimens

Described herein are a variety of methods for selecting and optimizing (and optionally administering) a treatment for a subject having or at risk of having a glomerular disease (e.g., FSGS) based on the presence or absence of a variant associated with increased risk of FSGS as described herein. For example, determining that a subject has one or more mutations, e.g., missense mutations, in an INF2 gene as described herein can confer a vastly increased risk (e.g., from 1/5000 to about 75-80% risk) of FSGS (an "increased risk" as used herein refers to a risk level that is above the risk of a person in the general population, e.g., who does not have a variant INF2 as described herein). The methods provided herein can include selecting a treatment regimen for a subject determined to have such risk for developing FSGS, based upon the absence or presence of a variant INF2 associated with FSGS as described herein.

In some embodiments, the methods include selecting a treatment for FSGS for subjects who have a variant INF2 as described herein, and thus have, or have an increased risk of developing, FSGS. In some embodiments, the treatment includes the administration of a treatment to a subject identified as at risk of developing FSGS, before the onset of any adverse event, e.g., before any clinical signs or symptoms of FSGS are present.

As used herein, the term "treat" or "treatment" is defined as the application or administration of a treatment regimen, e.g., one or more therapeutic agent or modality, to a subject identified by a method described herein as having a variant INF2 and thus having FSGS, or at risk of developing (i.e., a predisposition toward) FSGS. The treatment can be to cure, heal, alleviate, relieve, alter, remedy, ameliorate, palliate, delay progression of, reduce risk of, improve or affect FSGS, glomerular disease, or kidney function (e.g., GFR). For example, a standard therapeutic regimen for FSGS can include administering an angiotensin-converting enzyme (ACE) inhibitor (e.g., lisinopril), administering a corticosteroid medicament (e.g., prednisone, cortisone, hydrocortisone), administering an immunosuppressive agent (e.g., cyclosporine, tacrolimus, mycophenolate mofetil, azathioprine, mycophenolic acid), administering an alkylating agent (e.g., cyclophosphamide), administering an agent to lower blood pressure, administering an agent to promote podocyte repopulation, and/or promoting a low-sodium diet.

The methods can be used, for example, to optimize treatment or choose between alternative treatments (e.g., a particular dosage, mode of delivery, time of delivery) based on the risk assessment methods described herein. In some embodiments, treatment for a subject having or at risk for developing FSGS is selected based on the presence of a variant in the subject, and the treatment is administered to the subject. In some embodiments, various treatments or combinations of treatments can be administered based on the presence in a subject of a variant as described herein. Various treatment regimens are known for treating FSGS including, for example, regimens as described herein.

In some cases, methods of determining a treatment regimen and/or methods of treating or preventing FSGS can further include the step of monitoring the subject, e.g., for a change (e.g., an increase or decrease) in one or more of the diagnostic criteria for FSGS identified herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

In some embodiments, the methods for selection of a treatment regimen described herein also include evaluating other risk factors associated with glomerular disease as known in the art or described herein. Therefore, the methods of the invention can include selecting a treatment regimen for a subject having one or more risk factors for FSGS, and having a variant INF2 as described herein. The methods also can include administering a treatment regimen to a subject having, or at risk for developing, FSGS to thereby treat, prevent, or delay further progression of the disease. Exemplary risk factors for FSGS and other renal disorders include hypertension (e.g., blood pressure <130/80 mmHg), dyslipidemia (e.g., low-density lipoprotein cholesterol <100 mg/deciliter), proteinuria, glomerular hyperfiltration, hyperglycemia, smoking, and a high-sodium diet.

Also included herein are methods for identifying optimal treatments for subjects who have an increased risk of FSGS, to determine the effectiveness of a particular therapeutic intervention (e.g., a pharmaceutical or non-pharmaceutical intervention as described herein), and to alter the intervention to (1) reduce the risk of developing adverse outcomes and (2) enhance the effectiveness of the intervention. Thus, in addition to diagnosing or confirming the predisposition to FSGS, the methods described herein can be used to design a clinical trial to evaluate and optimize treatments for these subjects. For example, subjects in a clinical trial may be stratified, selected, classified, or categorized according to the presence or absence of a variant INF2 as described herein, and methods known in the art used to identify a statistically significant association between one or more of the specific variants (or of the simple presence of any variant) and responsiveness to a treatment.

Within the clinical trial setting, a theranostic method can provide key information to optimize trial design, monitor efficacy, and enhance drug safety. For instance, "trial design" theranostics can be used for subject stratification, determination of subject eligibility (inclusion/exclusion), creation of homogeneous treatment groups, and selection of subject samples that are representative of the general population. Such theranostic tests can therefore provide the means for subject efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a variant as described herein and any measurable or quantifiable parameter relating to the outcome of the treatment, e.g., efficacy (the results of which may be binary (i.e., yes and no) as well as along a continuum), side-effect profile (e.g., metabolic dysfunction, cardiovascular disorders, movement disorders, or extrapyramidal symptoms), treatment maintenance and discontinuation rates, return to work status, hospitalizations, total healthcare cost, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low total healthcare cost, favorable response to non-pharmacological treatments, and/or acceptable dose response curves) and the presence of a variant associated with FSGS (e.g., a specific variant) can influence treatment such that the treatment is recommended or selected for a subject having the selected variant.

Communicating Risk Assessment

In some embodiments, the methods described herein are used to assist medical or research professionals in diagnosing a subject with FSGS or determining a subject's risk of developing FSGS. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining whether specific variants are present in a biological sample from a subject, and (2) communicating information about the variants to that professional.

After information about the presence of a variant, e.g., identifying the specific variants present in the subject (and optionally about the subject's risk of developing FSGS, based on the presence or absence of one or more variants) is reported, a medical professional can take one or more actions that can affect subject care. For example, a medical professional can record information in the subject's medical record regarding the subject's risk of developing FSGS, or likely response to a given treatment for FSGS. In some cases, a medical professional can record information regarding a treatment assessment, or otherwise transform the subject's medical record, to reflect the subject's current treatment.

In some embodiments, a medical professional initiates or modifies a treatment after receiving information regarding the presence of a variant INF2 in a subject, for example. In some cases, a medical professional can recommend a change in therapy based on the presence of a variant INF2 in a subject (for example, initiating a therapy that will reduce the risk of FSGS based on the presence of a variant INF2 in the subject). In some cases, a medical professional can enroll a subject in a clinical trial for, by way of example, detecting correlations between a variant INF2 as described herein and any measurable or quantifiable parameter relating to the outcome of the treatment as described above.

A medical professional can communicate information regarding a subject's diagnosis or risk of FSGS to a subject or a subject's family. In some cases, a medical professional can provide a subject and/or a subject's family with information regarding FSGS and assessment information, including treatment options, prognosis, and referrals to specialists. In some cases, a medical professional can provide a copy of a subject's medical records to a specialist.

Any appropriate method can be used to communicate information to another person (e.g., a professional). For example, information can be given directly or indirectly to a professional. For example, a laboratory technician can input information regarding a subject's variant INF2 as described herein into a computer-based record. In some cases, information is communicated by making a physical alteration to medical or research records. For example, a medical professional can make a permanent notation or flag a medical record for communicating the presence or absence of a variant INF2 in a subject to other medical professionals reviewing the record. In addition, any type of communication can be used to communicate genetic and/or treatment information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

Nucleic Acids, Proteins, Probes, Primers, Antibodies, and Kits

Also within the scope of the present invention are isolated mutant INF2 nucleic acids and proteins, and agents for the detection of mutations in INF2 as described herein, including oligonucleotides (probes and primers) and antibodies.

INF2 Variant Nucleic Acids

Described herein are isolated INF2 variant nucleic acids that include one or more mutations described herein. The term "isolated nucleic acid molecule" includes nucleic acid molecules that are separated from other nucleic acid molecules that are present in the natural source of the nucleic acid. For example, in various embodiments, the isolated nucleic acid molecule can contain less than about 0.1 kb of 5' and/or 3' untranslated nucleotide sequences which naturally flank the nucleic acid molecule, e.g., in the mRNA. Moreover, an "isolated" nucleic acid molecule, such as a cDNA molecule, is substantially free of other cellular material, or culture medium when produced by recombinant techniques, or substantially free of chemical precursors or other chemicals when chemically synthesized.

In some embodiments, the variants have a sequence as shown in SEQ ID NOs.9 or 10, incorporating one or more variants as shown in SEQ ID NOs. 1-8, and encode a variant INF2 protein that includes one or more mutations described herein, e.g., L198R, R218W, R214H, S186P, E184K, R218Q, E220K, and/or L42P.

Also provided herein are vectors, e.g., expression vectors, that contain a nucleic acid encoding a variant INF2 described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

Probes and Primers

Thus included herein are probes and primers that hybridize with a region of human INF2 as described herein, as well as antibodies that bind specifically to a mutant INF2 protein (and do not bind substantially to a wild-type INF2); these probes, primers, and antibodies can be used to detect a variant described herein.

Typically a probe/primer is an isolated or purified oligonucleotide. The oligonucleotide typically includes a region of nucleotide sequence that hybridizes under stringent conditions to at least about 15 consecutive nucleotides of a sense or antisense sequence of a sequence set forth herein, e.g., SEQ ID NOs: 1-10. In some embodiments, the oligonucleotide comprises about 20, 25, 30, 35, 40, 45, 50, 55, 60, 65, or 75 consecutive nucleotides of a sequence set forth herein, e.g., SEQ ID NOs: 1-10.

In some embodiments, the nucleic acid is a probe which is at least 10, and less than 200 (typically less than about 100 or 50) base pairs in length. It should be identical to, or differ by 1, or less than 1 in 5 or 10 bases, from a sequence disclosed herein, e.g., SEQ ID NOs: 1-10, e.g., to a wild type or variant sequence. If alignment is needed for this comparison the sequences should be aligned for maximum homology. "Looped" out sequences from deletions or insertions, or mismatches, are considered differences.

In some embodiments a set of primers is provided, e.g., primers suitable for use in a PCR, which can be used to amplify a selected region of an INF2 variant sequence, e.g., to detect the presence of one or more variants. The primers should be at least 20 base pairs in length and less than about 100 base pairs in length. The primers should be identical, or differ by one base from a sequence disclosed herein or from a naturally occurring variant. For example, suitable primers include a pair of primers that selectively amplify a region between SNPs rs3783397 (at approximately 103 Mb or 115.7 cM on the Marshfield map) and rs657621 (at approximately 106 Mb or 119.3 cM). For example, in some embodiments one of the pair of primers includes a sequence that is identical to at least 20 bp of ss43578679 (or the complement thereof), and the other primer includes a sequence that is identical to at least 20 bp of ss90077099 (or the complement thereof), such that the two primers amplify the region between rs3783397 and rs657621.

INF2 Variant Proteins

Also included herein are variant INF2 proteins that have the sequence of SEQ ID NO:20 and include one or more mutations described herein, e.g., L198R, R218W, R214H, S186P, E184K, R218Q, E220K, and/or L42P (see FIG. 6), and fragments thereof including these mutations, e.g., for use as immunogens to raise and test antibodies that bind specifically to the mutant form of the protein. Variant INF2 protein can be isolated from cells or tissue sources using standard protein purification techniques. INF2 variant proteins or fragments thereof can be produced by recombinant DNA techniques or synthesized chemically.

In some embodiments, the INF2 variant proteins are in a fusion protein, e.g., with a non-INF2 sequence such as a detectable peptide (such as GFP or a variant thereof) or a peptide useful in purifying the protein, e.g., GST, HA, or 6-His.

Anti-INF2 Variant Antibodies

The term "antibody" as used herein refers to an immunoglobulin molecule or immunologically active portion thereof, i.e., an antigen-binding portion. Examples of immunologically active portions of immunoglobulin molecules include F(ab) and F(ab')2 fragments which can be generated by treating the antibody with an enzyme such as pepsin.

The antibody can be a polyclonal, monoclonal, recombinant, e.g., a chimeric or humanized, fully human, non-human, e.g., murine, bispecific, monospecific, or single chain antibody. In some embodiments it has effector function and can fix complement. The antibody can be coupled, e.g., to a detectable agent.

The antibodies are generated using methods known in the art; see, e.g., Lo, *Antibody Engineering: Methods and Protocols* (Methods in Molecular Biology), Humana Press: 1 edition (Dec. 5, 2003).

Kits

In some embodiments, one, two, or more INF2 variant nucleic acids or proteins, or probes and/or primers, or antibodies for detecting variants described herein, can be combined with packaging material in a kit. The kits can include one or more other elements including: instructions for use; and other reagents such as a label or an agent useful for attaching a label to a probe, primer, or antibody, and/or reagents for detecting the specific binding of the probe, primer, or antibody to a variant INF2, and thus for detecting the presence of the variant INF2. Instructions for use can include instructions for applications of the kit for diagnosing or assessing risk of FSGS in a method described herein. Other instructions can include instructions for attaching a label to the probe, primer, or antibody; instructions for performing in situ analysis with the probe, primer, or antibody; and/or instructions for obtaining a sample to be analyzed from a subject. In some cases, the kit can include a labeled probe or primer that hybridizes to a region of human chromosome as described herein, or a labeled antibody that binds to a mutant INF2 protein as described herein. In some embodiments, the kit includes a mutant INF2 protein or nucleic acid as a reference.

In some embodiments, kits for use in self-testing are provided. Such test kits can include devices and instructions that a subject can use to obtain a biological sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

The invention will be further described in the following examples, which do not limit the scope of the invention described in the claims.

EXAMPLES

Example 1—Genotype Analysis of FSGS Families

Subjects were enrolled in these studies after obtaining informed consent in accordance with a human subjects protocol approved by the Brigham and Women's Hospital and other relevant institutions. Genomic DNA was extracted from peripheral blood. Urine microalbumin and creatinine concentrations were measured, and clinical and family history information was collected for each subject. Medical records, kidney biopsies, and biopsy reports were reviewed when available.

Members of a large family with apparent autosomal dominant FSGS were genotyped using a dense set of SNP markers (Affymetrix 250K SNPChip array) followed by focused microsatellite genotyping. In family FGBR, a genome-wide analysis was performed using DNA samples from 31 informative family members and approximately 300 microsatellite markers from the Marshfield map using standard methodology. Parametric 2-point and multipoint lod scores were computed using the FASTLINK and VITESSE programs (Schaffer, *Hum. Hered.* 46:226-35 (1996); O'Connell & Weeks, *Nat. Genet.* 11:402-8 (1995)). In family FGJN, genome-wide linkage analysis was performed using 250K Affymetrix SNPChips. Follow-up genotyping was performed using 14q microsatellite markers, and parametric multipoint linkage analysis was performed using both LINKAGE and GENEHUNTER genetic algorithms (Markianos et al., *Am. J. Hum. Genet.* 68:963-77 (2001)). A locus for FSGS was identified in this family on 14q32 (family FGJN, FIG. 1B). This region overlapped with a larger locus previously identified by linkage analysis using microsatellite markers in another large family with a similar clinical course (family FGBR, FIG. 1A). Because of the phenotypic similarity between these families, it was suspected that FSGS in both families was caused by a defect in the same gene. Under this assumption, the critical region was defined by flanking SNPs rs3783397 (at approximately 103 Mb or 115.7 cM on the Marshfield map) and rs6576201 (at approximately 106 Mb or 119.3 cM). No other suspicious loci were identified in these genome scans in either family.

Additional genotyping of the identified variants was performed using MALDI-TOF mass spectrometry (Sequenom) at the Harvard-Partners Core Genotyping Facility. Using standard Sanger sequencing methodology on an ABI 3730 machine, PCR-amplified segments containing coding sequence and flanking splice sites of 15 genes were sequenced (INF-2, ADSSL1, SIVA1, AKT1, PLD4, AHNAK2, CDCA4, GPR132, JAG2, NUDT14, BRF1, PACS2, MTA1, CRIP2, CRIP1) from the 14q critical region in 12 individuals, 3 affected and 3 unaffected members from family FGBR and from family FGJN, followed by additional sequencing of INF2 in family members and control individuals. A sequence variant was observed in each family within the same exon of INF2 that segregated with disease and predicted a non-conservative amino-acid change (R218Q in FGJN and S186P in FGBR). No significant sequence variants were observed in any of the fourteen other genes analyzed. The R218Q variant found in family FGJN was a de novo mutation, as the first individual in the family carrying this R218Q variant shared the disease associated haplotype, but not this variant, with several unaffected siblings.

Figure 1B:
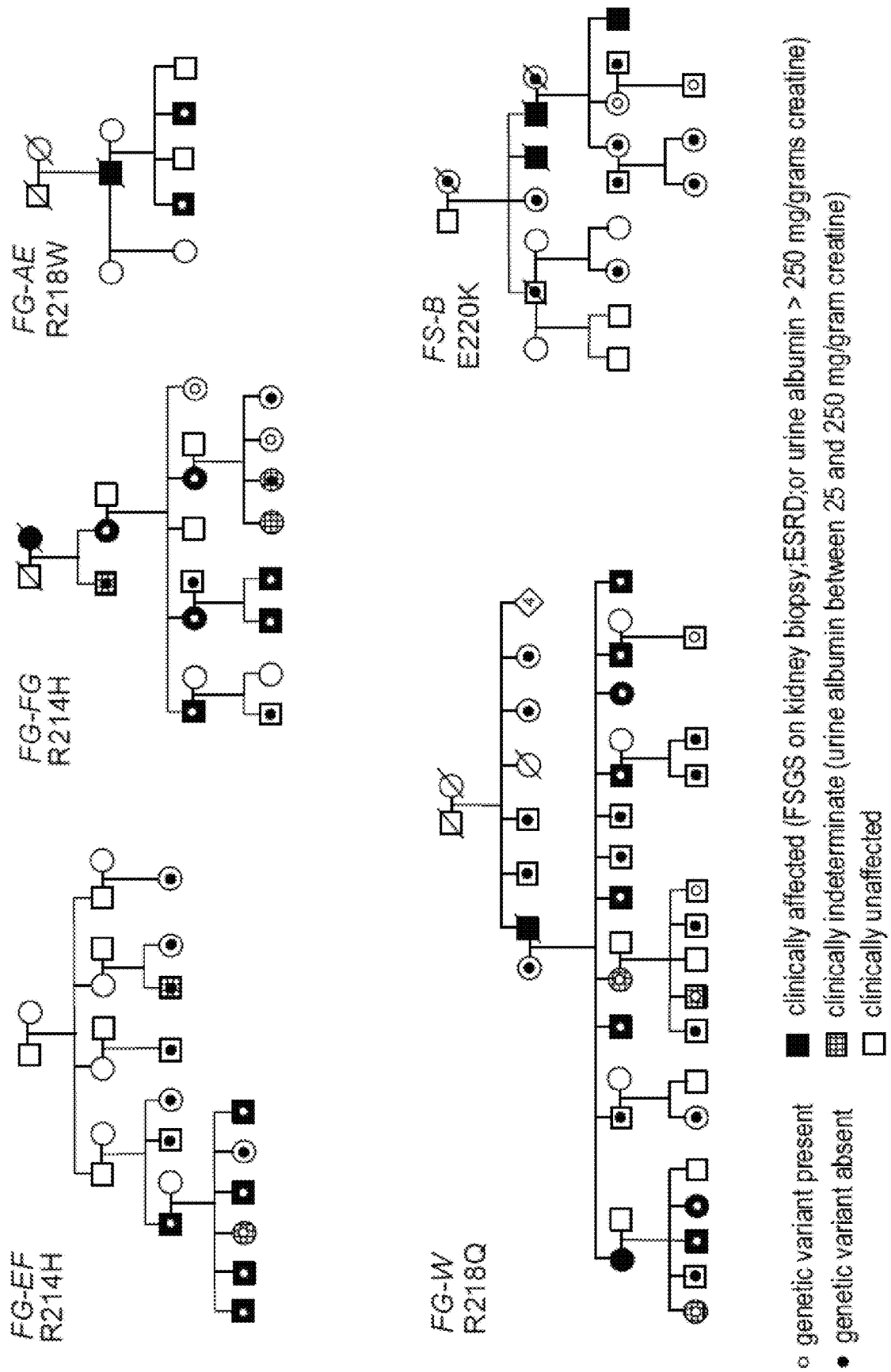
Figure 2B:
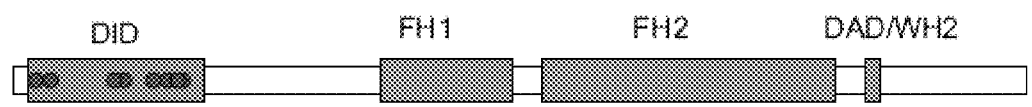

INF2 was sequenced for 91 unrelated individuals with familial FSGS. In probands from nine of these families, point mutations predicted to lead to non-conservative amino acid changes were identified (Table 2, FIG. 2A). These variants were typed in all available family members. A family member was considered to be definitely affected if he or she had kidney biopsy proven FSGS, end-stage renal disease (ESRD) without other apparent cause, or significant albuminuria without other apparent cause (>250 mg albumin per gram creatinine in a urine sample). These mutations segregated with disease in their respective families (FIGS. 1A-B). In five of the families, some of the younger individuals carrying these point mutations had no increase in urine protein excretion, consistent with an autosomal dominant disease with reduced, age-related penetrance, and similar to the TRPC6 and ACTN4-associated phenotypes. Several additional nucleotide variants were seen in exons 8, 18, and 20, but these did not segregate with disease and were also found in control individuals. All of the disease segregating mutations are located within a single functional region of INF2 known as the diaphanous-inhibitory domain, or DID (FIG. 2B), and most reside within exon 4.

TABLE 2

Point Mutations Predicted to Cause
Non-conservative Amino Acid Changes

| Family | Ethnicity (Geography) | Mutation | Age range at diagnosis (n = number of affecteds with clinical data) | Age range at ESRD onset (n = number with ESRD) |
|---|---|---|---|---|
| FGBR | Caucasian (Canada) | S186P | 12-67 (n = 13) | 32-67 (n = 6) |
| FGDM | Caucasian (Ireland/USA) | L198R | 13-18 (n = 2) | 21-29 (n = 2) |
| FGEA | African-American (USA) | R218W | 27-33 (n = 3) | 30-40 (n = 3) |
| FGEF | Caucasian (USA) | R214H | 19-35 (n = 5) | 49 (n = 1) |
| FGEP | Caucasian (USA) | L42P | 11-13 (n = 3) | 13-14 (n = 3) |
| FGER | Caucasian (Canada) | S186P | 13-60 (n = 9) | 20-50 (n = 6) |
| FGFG | Caucasian (USA) | R214H | 12-72 (n = 7) | 17-60 (n = 3) |
| FGGN | Latino (Mexico) | A13T | 21 (n = 1) | n = 0 |
| FGGY | African-American (USA) | E184K | 17-30 (n = 7) | 17-30 (n = 7) |
| FGJN | Caucasian (USA) | R218Q | 22-45 (n = 10) | 30-45 (n = 4) |
| FSB | Caucasian (USA) | E220K | 13-21 (n = 5) | 23-30 (n = 4) |

To be certain that these variants did not represent normal sequence variants, and also to be certain that the INF2 gene is not simply a site of frequent but biologically insignificant variant, exon 4, the location of all but two of the putative mutations, was resequenced in 282 control individuals. None of these control individuals carried any of these putative disease-causing INF2 variants, nor any other missense or splicing variant. The other two putative disease-causing mutations found in exon 2 (A13T, L42P) were genotyped as well as the E184K and R218Q mutations in an additional 341 control individuals using Sequenom genotyping assays. Neither variant was present in any of the 682 chromosomes assayed. These data verify that neither these mutations, nor other non-synonymous DID variants, are present in control groups.

Phenotypes in families with the described INF2 mutations share certain features. Unlike the early onset, nephrotic presentation typically seen with mutations in both alleles of the genes encoding slit-diaphragm proteins nephrin and podocin, these individuals presented in early adolescence or adulthood, typically with only moderate proteinuria. While nephrotic range proteinuria was documented in members of several of these families, none of the affected individuals had evidence of the full spectrum of clinical findings that constitutes the so-called nephrotic syndrome. Microscopic hematuria was noted in a subset of the affected individuals. Hypertension was a common but not universal feature of the affected individuals. Similar to what has been observed in subjects with dominantly inherited mutations in ACTN4, disease and proteinuria in the affected individuals were progressive, often leading to ESRD.

Figure 3A:
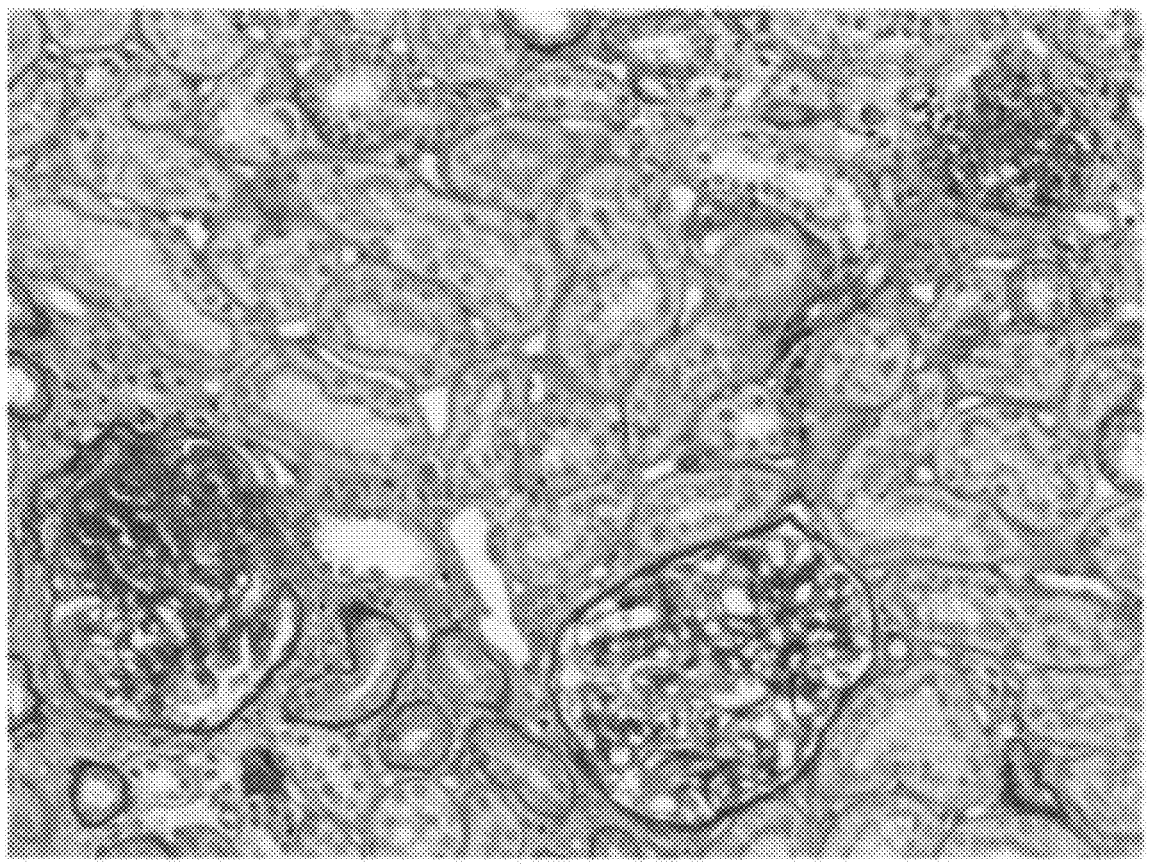
FIGS. 3A-C are histopathology images for affected family members from family FSB (3A, 3B) and FGJN (3C).
Figure 3B:
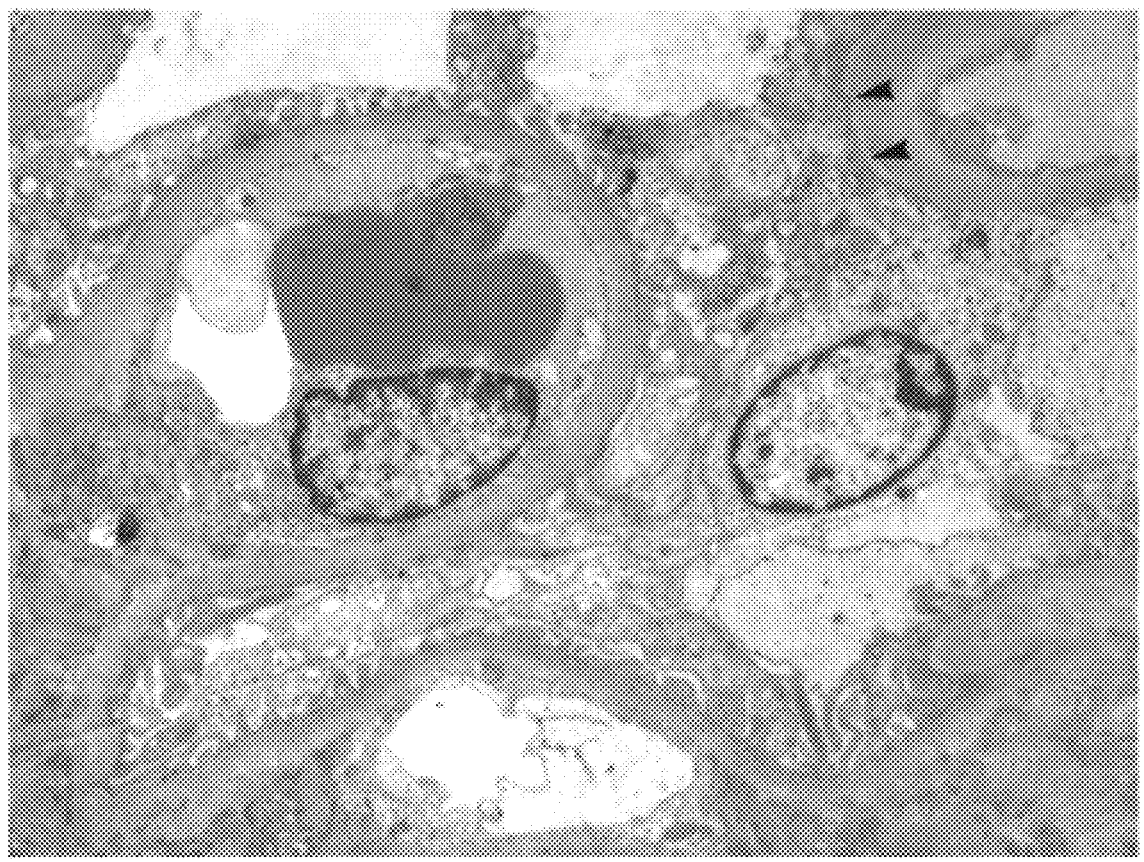
Figure 3C:
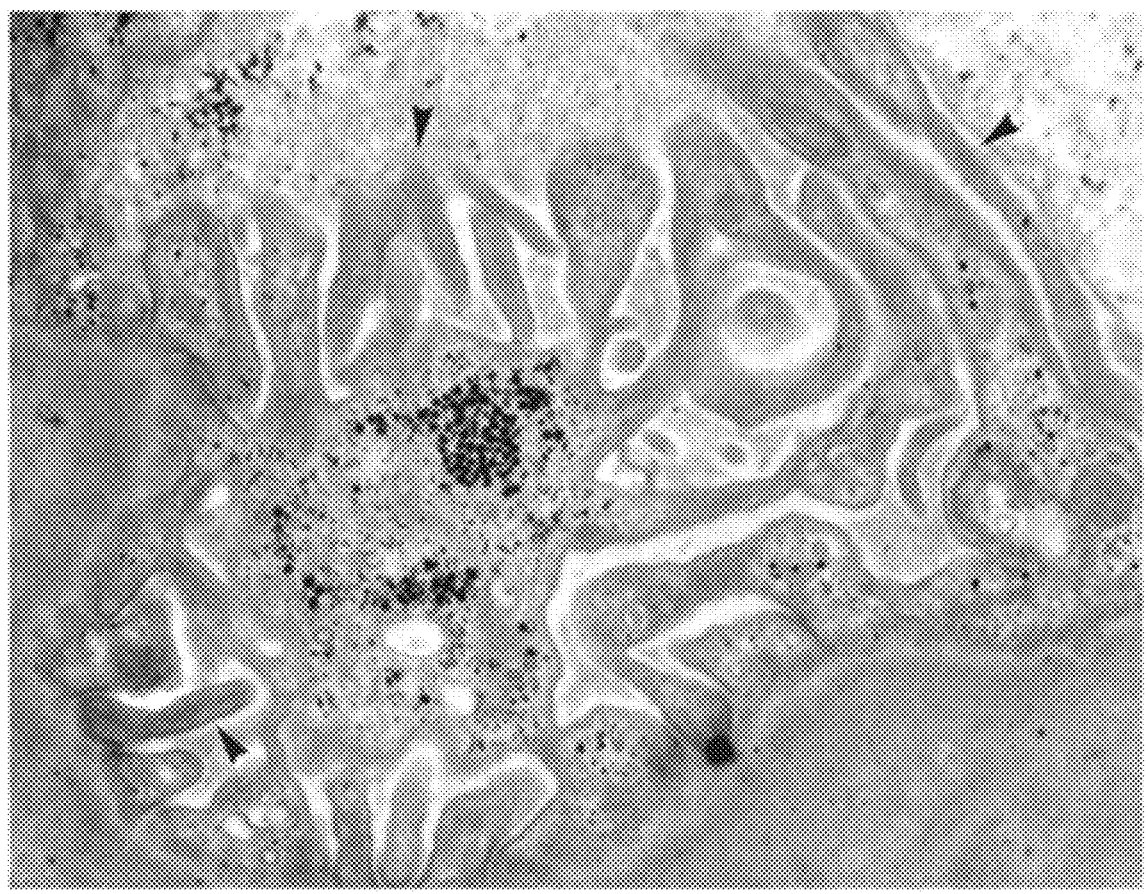

The histopathological findings in available renal biopsy tissue samples from individuals with INF2 mutations were reviewed. Light microscopy typically showed focal and segmental glomerulosclerosis (FIG. 3A). Electron microscopy of kidney biopsy material from an INF2-mutant FSGS subject showed focal areas of podocyte foot process effacement, typical of secondary and some genetic forms of FSGS, as well as areas where the foot processes and slit-diaphragms were well preserved. Unusually prominent actin bundles within the foot processes were also noted (FIG. 3B). Glomerular hypertrophy was not a prominent feature of the biopsies. None of the original pathology reports noted perihilar, collapsing, or cellular lesions that characterize some histological subtypes of FSGS, nor were any such lesions observed here. Thus, these biopsies would be categorized as "FSGS, not-otherwise-specified" following one widely adopted classification scheme. D'Agati et al., *Am. J. Kidney Dis.* 43:368-82 (2004).

In sum, these data demonstrate genetic linkage in two large families to a region on chromosome 14 containing INF2. Missense mutations in INF2 in 11 of 93 families examined cause non-conservative substitutions in amino acids that are highly conserved through evolution. Thus, within the individual families harboring these mutations, inheritance of the mutation segregates with disease.

Example 2—Structural Model of INF2

INF2 is a member of the formin family of actin-regulating proteins that accelerate actin polymerization. For review, see Faix and Grosse, *Dev. Cell* 10:693-706 (2006). As noted, all of the FSGS-associated mutations that were identified lie within the DID. The DID is an autoinhibitory domain found in the sub-set of diaphanous formins. In the best studied diaphanous formin, mDia1, the interaction of the N-terminal DID with the C-terminal diaphanous activating domain (DAD) inhibits mDia1 function; this inhibition is relieved by binding to Rho. Structural data available for the N-terminal region of mDia1 was used to map the mutated INF2 residues and to make functional predictions. Structural models of INF2 were designed using the Phyre resource from Imperial College, London. See Kelley et al., *Nat. Protoc.* 4:363-71 (2009). Amino acids 1-424 of mouse INF2 were submitted, and INF2 models based on the structural coordinates of three mDia1 N-terminal structures were recovered. The fourth mDia1 N-terminal structure was not represented in this search. The models were manipulated using the program PyMOL. In the model, the identified FSGS mutations correspond to the following residues in mDia1 in the structural alignment (Table 3).

TABLE 3

Structural Alignment of INF2 and mDia1 Residues

| INF2 Residue | mDia1 Residue |
|---|---|
| A13 | V116 |
| L42 | L143 |
| E184 | G292 |
| S186 | K294 |
| L198 | L306 |
| R214 | R322 |
| R218 | R326 |
| E220 | E328 |

Figure 2C:
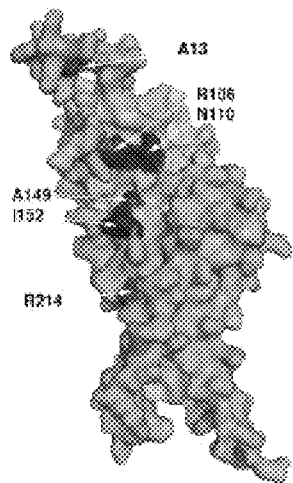
Figure 2D:
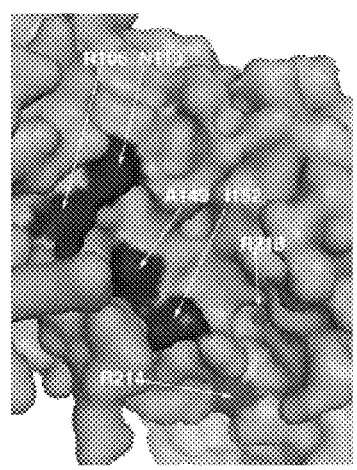
Figure 2E:
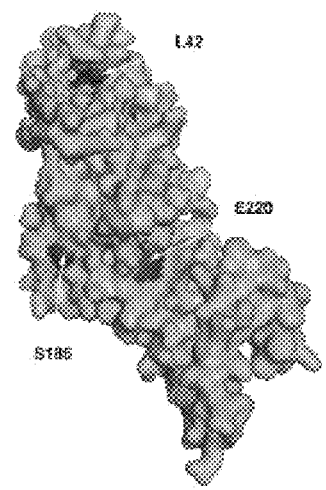

The INF2 model derived from the mDia1-RhoC structure (FIGS. 2C-E) was in general agreement with models derived from the other available mDia1 structures. See Rose et al., *Nature* 435:513-8 (2005). Two mutated residues, R214 and R218, lie close to the DAD-binding region of the DID. R214 is on the surface of the DID in proximity to this site (FIG. 2C). R218 is predominately buried, but has a small region of surface exposure in this region (FIG. 2D). Three other mutated residues (L42, S186, E220) are surface-exposed but on the opposite side of the DID structure from the DAD-binding region (FIG. 2E). The A13 position is surface-exposed and lies at the N-terminus of the DID, in the region corresponding to the GBD (GTPase binding domain) of mDia1. Two of the mutated residues are buried in the core DID structure (E184, L198).

Based on these models, it was postulated that potential functions for the mutated INF2 residues. R214 and R218 likely form part of the DAD binding site, given their spatial proximity to key DAD-binding residues A149 and I152. The prominent exposure of L42, S186, and E220 on the DID surface raises the possibility that they interact with other molecules. Since the N-terminus of mDia1 plays a major role in its cellular localization, the N-terminus of INF2 could also mediate localization. It also can be postulated that E184, L198, and R218 are likely to be important for maintaining the overall fold of the DID. These residues are buried in the interior in all of the models. Accordingly, the identified mutations (E184K and L198R, R218Q) could have dramatic effects on the integrity of the DID.

Example 3—INF2 Expression Analysis

Figure 4A:
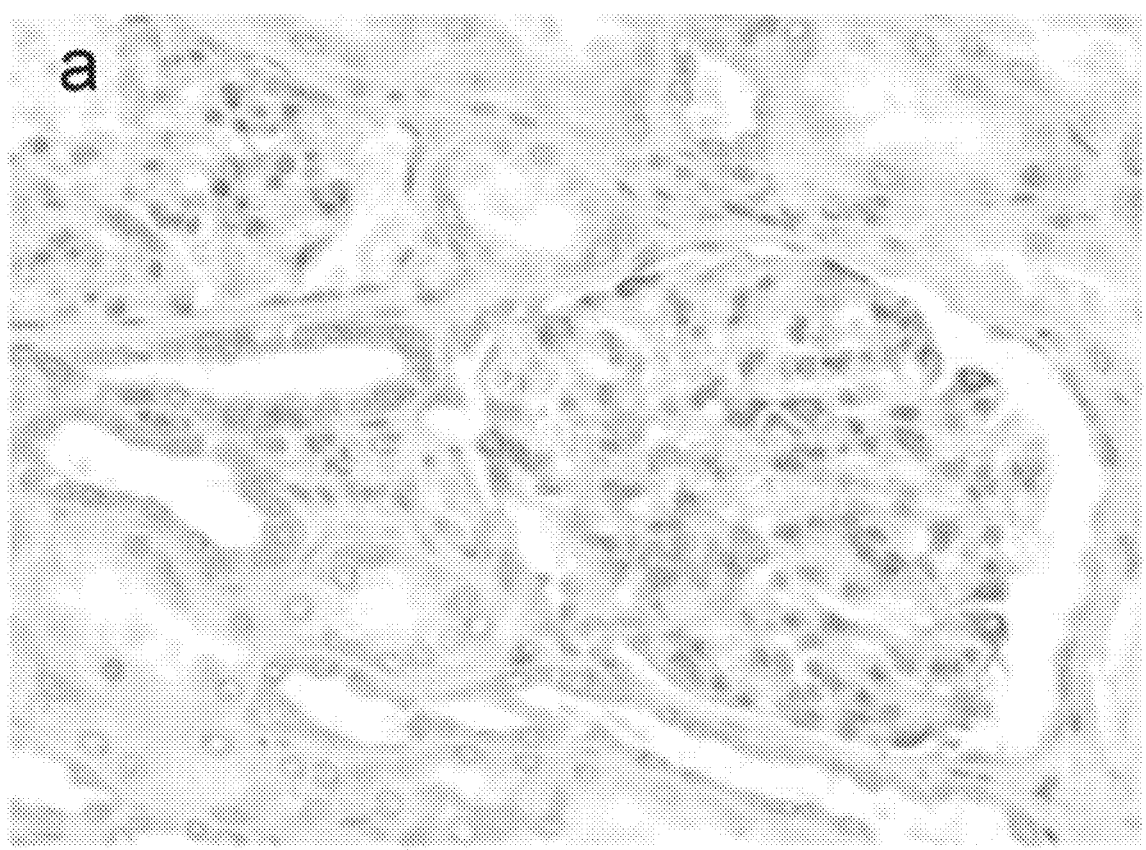
FIGS. 4A-B are photomicrographs demonstrating INF2 expression in various tissues.
Figure 4B:
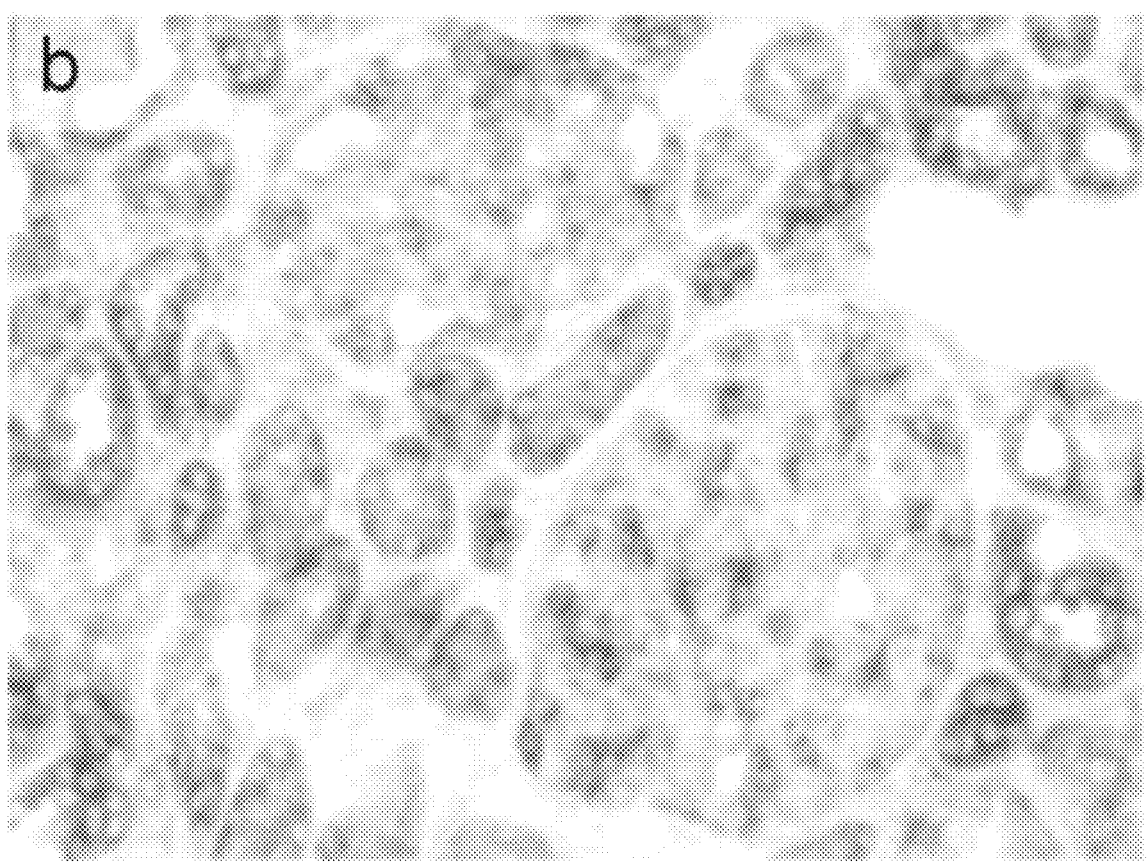

The pattern of expression of INF2 in the kidney was studied by non-radioactive in situ hybridization and by antibody staining (FIGS. 4A-B). Frozen sections (10 µm) of human kidney tissue were cut in a cryostat and captured onto Superfrost plus microscope slides (Fisher Scientific, Pittsburgh, PA). Sections were then fixed and acetylated, and hybridized to the probe at 70° ° C. for approximately 72 hours (approximate concentration of 100 ng/ml). Non-radioactive in situ hybridization was performed as described by Berger et al., *J. Comp. Neurol.* 433:101-14 (2001), using a digoxigenin (DIG)-labeled cRNA probe that contained the first 590 bases of the INF2 sequence. Hybridized probe was visualized using alkaline phosphatase-conjugated anti-DIG Fab fragments (Roche, Indianapolis, IN) and 5-Bromo-4-chloro-3-indolyl-phosphate/Nitroblue tetrazolium (BCIP/NBT) substrate (Kierkegard and Perry Laboratories, Gaithersburg, MD). Sections were rinsed several times in 100 mM Tris, 150 mM NaCl, 20 mM EDTA pH 9.5, and coverslipped with glycerol gelatin (Sigma, St. Louis, MO). Control sections were incubated in an identical concentration of the sense probe transcript. Both showed INF2 expression in the podocyte.

Expression of INF2 and the slit-diaphragm protein nephrin were also examined together (FIG. 4B). Five micron sections of acetone fixed kidneys from healthy 6-week old mice were made. After washing with phosphate-buffered saline, sections were incubated with primary antibodies: rabbit anti-INF2 (C-terminal 300 amino acids), guinea pig anti-nephrin (Progen Biotechnik). The rabbit anti-INF2 antibody was as described by Chhabra et al., *J. Cell Sci.* 122:1430-40 (2009). Anti-rabbit Cy2 coupled and anti-guinea pig Cy3 coupled secondary antibodies were used to visualize INF2 and nephrin, and DAPI was used to visualize nuclei. Specimens were analyzed using a Nikon TE-200E inverted microscope and AutoDeblur deconvolution software (Media Cybernetics). INF2 expression showed some areas of colocalization with nephrin in podocytes. Some INF2 staining was also noted in a pericapillary pattern, suggesting expression in cells other than podocytes. Within the podocyte, antibody staining showed what appeared to be a predominantly perinuclear pattern of INF2.

Figure 4C:
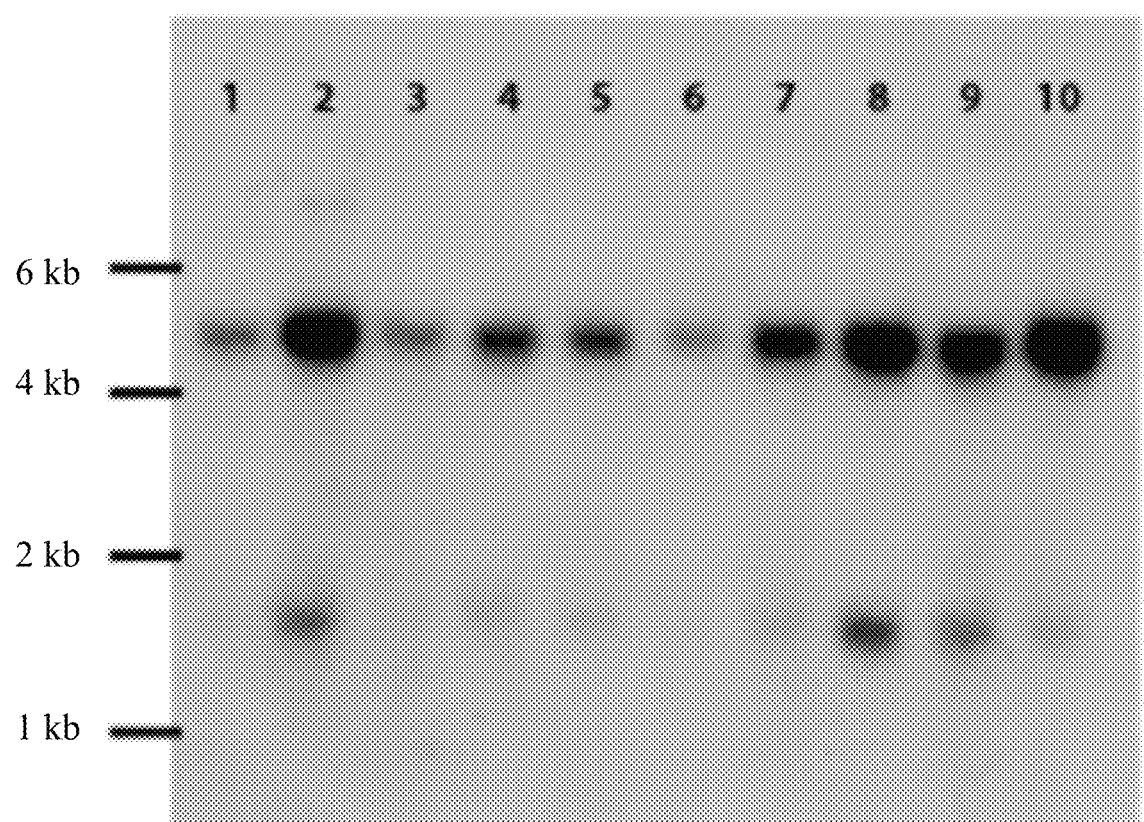
FIG. 4C is a picture of a Northern blot. Gel lanes: 1, Brain; 2, Placenta; 3, Skeletal muscle; 4, Heart; 5, Kidney; 6, Pancreas; 7, Liver; 8, Lung; 9, Spleen; 10, Colon.

Northern blot analysis also was performed. A human multiple-tissue Northern blot was purchased from Ambion. 5' sense and antisense probes consisting of the first 590 basepairs of INF2 were made using $\alpha^{32}$P-dCTP labeling of a PCR generated fragment using Klenow (New England Biolabs NEBlot kit). Northern blot analysis showed strong INF2 expression in all tissues tested, and identified INF2 transcripts of approximately 1.5 and 4.5 kb in length (FIG. 4C). This was consistent with previous reports describing INF2 as well as the major transcripts predicted from ESTs and genomic sequence analysis as collated in the UCSC Genome Browser (genome.ucsc.edu on the World Wide Web).

Example 4—INF2 Mutagenesis

To assay for effects of two mutations (E184K and R218Q) on the structural integrity of the DID, a clone containing full-length INF2 in the pCMV6-XL5 vector (Origene) was obtained. Mutagenesis was carried out using the Stratagene QuikChange II kit and mutagenesis primers designed to insert the E184K, S186P (a third mutation located away from the DAD binding site), and R218Q mutations into the INF2 cDNA. All mutagenesis reactions were verified by sequencing. These three mutations included the two (E186P and R218Q) found in the large families used in the initial genetic linkage analysis.

Undifferentiated human podocytes in culture were transfected with wild-type or mutant INF2 (E184K, S186P, and R218Q) constructs using FuGENE (Roche). An antibody to the C-terminus of INF2 directly conjugated to Cy3, a water-soluble fluorescent dye of the cyanine dye family, was used for visualizing wild-type and mutant INF2 protein at 1:200 dilutions. FITC Phalloidin and DAPI were to visualize actin filaments and nuclei, respectively.

Wild-type transfected podocytes showed perinuclear INF2 staining, while INF2 harboring E184K and R218Q mutations showed a different localization pattern, with a finer, more diffuse distribution. The cellular localization of the S186P mutant INF2 was closer to the pattern observed in the wild-type cells, but with a more vermiform appearance. Both the wild-type and mutant forms of INF2 showed significant co-staining with phalloidin, consistent with the notion that these proteins induced prominent actin polymerization at their localization, with the overall staining of phalloidin mimicking that of INF2. In the mutant transfected cells, stress fibers and cortical actin were less prominent. The similar and more dramatic changes seen with the E184K and R218Q mutants are consistent with the predicted effect on the overall INF2 DID structure. Furthermore, these data suggest that the DID domain is critical for the proper subcellular localization of INF2, and is consistent with previous data demonstrating that it is not required for the ability of INF2 to mediate actin polymerization. See, e.g., Chhabra et al., *J. Cell Sci.* 122:1430-40 (2009).

While prominent actin filament bundles were noted in the electron micrographs, actin filaments appeared somewhat less prominent than normal in the INF2-mutant expressing cells.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a sample from a subject suspected of having a risk for developing focal segmental glomerulosclerosis (FSGS), the method comprising enriching the sample for inverted formin 2 (INF2) nucleic acid molecules by contacting the sample with a detectably labeled oligonucleotide that specifically binds to an INF2 nucleic acid having the sequence of SEQ ID NO: 21 comprising a mutation in at least one nucleotide position corresponding to a position selected from the group consisting of 736, 795, 784, 699, 693, 796, 801, and 268 of SEQ ID NO: 21, wherein the detectably labeled oligonucleotide comprises a sequence having at least 15 consecutive nucleotides of the sequence of the INF2 nucleic acid or a complementary sequence thereof, and wherein the sequence of the detectably labeled oligonucleotide comprises the mutation.

2. The method of claim 1, wherein the mutation in the INF2 sequence comprises a missense mutation in the INF2 coding sequence.

3. The method of claim 1, wherein the mutation in the INF2 sequence results in a nonconservative amino acid substitution in the resulting protein sequence.

4. The method of claim 1, wherein the mutation changes an amino acid in the diaphanous inhibitory domain (DID) of INF2.

5. The method of claim 1, wherein the detectably labeled oligonucleotide is directly labeled.

6. The method of claim 5, wherein the detectably labeled oligonucleotide is directly labeled with a fluorophore.

7. The method of claim 1, wherein the detectably labeled oligonucleotide is indirectly labeled.

8. The method of claim 1, wherein the detectably labeled oligonucleotide is fixed to a solid support.

9. The method of claim 1, wherein the detectably labeled oligonucleotide is 15-1000 nucleotides long.

10. The method of claim 1, wherein the detectably labeled oligonucleotide is 15-200 nucleotides long.

11. The method of claim 1, wherein the detectably labeled oligonucleotide is 15-50 nucleotides long.

12. The method of claim 1, wherein the detectably labeled oligonucleotide comprises a sequence selected from any one of SEQ ID NOs: 1 to 8, wherein n of SEQ ID NO: 1 is g; n of SEQ ID NO: 2 is t; n of SEQ ID NO: 3 is a; n of SEQ ID NO: 4 is c; n of SEQ ID NO: 5 is a; n of SEQ ID NO: 6 is a; n of SEQ ID NO: 7 is a; and n of SEQ ID NO: 8 is c.

* * * * *

SEQUENCE LISTING

<160> NUMBER OF SEQ ID NOS: 41

<210> SEQ ID NO 1
<211> LENGTH: 21
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 11
<223> OTHER INFORMATION: n = t or g

<400> SEQUENCE: 1
gtcaccctgc ntagcgtgat c                                              21

<210> SEQ ID NO 2
<211> LENGTH: 21
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 10
<223> OTHER INFORMATION: n = c or t

<400> SEQUENCE: 2
acccagctgn ggaacgagtt t                                              21

<210> SEQ ID NO 3
<211> LENGTH: 15
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 8
<223> OTHER INFORMATION: n = g or a

<400> SEQUENCE: 3
cgcgcgcnca cccag                                                     15

<210> SEQ ID NO 4
<211> LENGTH: 18
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 7
<223> OTHER INFORMATION: n = t or c

<400> SEQUENCE: 4
gagctcnccg gcagcgac                                                  18

<210> SEQ ID NO 5
<211> LENGTH: 18
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 10
<223> OTHER INFORMATION: n = g or a

<400> SEQUENCE: 5

```
gtcatgaacn agctctcc                                                    18

<210> SEQ ID NO 6
<211> LENGTH: 18
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 8
<223> OTHER INFORMATION: n = g or a

<400> SEQUENCE: 6
cagctgcnga acgagttt                                                    18

<210> SEQ ID NO 7
<211> LENGTH: 18
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 10
<223> OTHER INFORMATION: n = g or a

<400> SEQUENCE: 7
ctgcggaacn agtttatc                                                    18

<210> SEQ ID NO 8
<211> LENGTH: 15
<212> TYPE: DNA
<213> ORGANISM: Artificial Sequence
<220> FEATURE:
<223> OTHER INFORMATION: synthetically generated oligonucleotides
<220> FEATURE:
<221> NAME/KEY: variation
<222> LOCATION: 8
<223> OTHER INFORMATION: n = t or c

<400> SEQUENCE: 8
cggctgcncc agatg                                                       15

<210> SEQ ID NO 9
<211> LENGTH: 812
<212> TYPE: DNA
<213> ORGANISM: Homo sapiens

<400> SEQUENCE: 9
atgtcggtga aggagggcgc acagcgcaag tgggcagcgc tgaaggagaa gctggggcca      60
caggattcgg accccacgga ggccaacctg gagagcgcgg accccgagct gtgcatccgg     120
ctgctccaga tgcccctctgt ggtcaactac tccggcctgc gcaagcgcct ggagggcagc    180
gacggcggct ggatggtgca gttcctggag cagagcggcc tggacctgct gctggaggcg    240
ctggcgcggc tgtcgggccg cggcgttgca cgtatctccg acgccctgct gcagctcacc    300
tgcgtcagct gcgtgcgcgc cgtcatgaac tcgcggcagg gcatcgagta catcctcagc    360
aaccagggct acgtgcgcca gctctcccag gccctggaca catccaacgt gatggtgaag    420
aagcaggtgt ttgagctact ggctgccctg tgcatctact ctcccgaggg ccacgtgctg    480
accctggacg ccctggacca ctacaagacg cgtgtgcagcc agcagtaccg cttcagcatt    540
gtcatgaacg agctctccgg cagcgacaac gtgccctacg tggtcaccct gcttagcgtg    600
```

```
atcaacgccg tcatcttggg ccccgaggac ctgcgcgcgc gcacccagct gcggaacgag      660
tttatcgggc tgcagctgct ggacgtcctg gctcgcctgc gagacctgga ggatgccgac      720
ctgctgatcc agctggaggc tttcgaggag gctaaggccg aggacgagga ggagctgctg      780
cgagtctctg gcggggtcga catgagcagc ca                                    812
```

<210> SEQ ID NO 10
<211> LENGTH: 4668
<212> TYPE: DNA
<213> ORGANISM: Homo sapiens

<400> SEQUENCE: 10

```
cgccccgcgc ccgccaggag ccaccgtccg agccttgcgg agcgcggcag tgggcgccgg       60
ctgcccgcag cccctgaccc ggccccggac ggagcgccgg ccgcaccacc gccctctggc      120
cgttgcctca ccggctcggc aagatgtcgg tgaaggaggg cgcacagcgc aagtgggcag      180
cgctgaagga gaagctgggg ccacaggatt cggaccccac ggaggccaac ctggagagcg      240
cggaccccga gctgtgcatc cggctgctcc agatgccctc tgtggtcaac tactccggcc      300
tgcgcaagcg cctggagggc agcgacggcg gctggatggt gcagttcctg gagcagagcg      360
gcctggacct gctgctggag gcgctggcgc ggctgtcggg ccgcggcgtt gcacgtatct      420
ccgacgccct gctgcagctc acctgcgtca gctgcgtgcg cgccgtcatg aactcgcggc      480
agggcatcga gtacatcctc agcaaccagg gctacgtgcg ccagctctcc caggccctgg      540
acacatccaa cgtgatggtg aagaagcagg tgtttgagct actggctgcc ctgtgcatct      600
actctcccga gggccacgtg ctgacccctgg acgccctgga ccactacaag acggtgtgca      660
gccagcagta ccgcttcagc attgtcatga cgagctctc cggcagcgac aacgtgccct      720
acgtggtcac cctgcttagc gtgatcaacg ccgtcatctt gggccccgag gacctgcgcg      780
cgcgcaccca gctgcggaac gagtttatcg gctgcagct gctggacgtc ctggctcgcc      840
tgcgagacct ggaggatgcc gacctgctga tccagctgga ggctttcgag gaggctaagg      900
ccgaggacga ggaggagctg ctgcgagtct ctggcggggt cgacatgagc agccaccagg      960
aggtctttgc ctccctgttc cacaaggtga gctgctcccc ggtgtctgcc cagctcctgt     1020
cggtgctgca gggcctcctg cacctggagc ccaccctccg ctccagccag ctgctctggg     1080
aggccctgga gagcctcgtg aaccgggccg tgctcctggc cagcgatgcc aggaatgca     1140 ccctggagga agtggttgag cggctcctgt ctgtcaaggg gcgacccaga ccgagccccc     1200
tggtcaaggc ccataaaagc gtccaggcca acctagacca gagccagagg ggcagctccc     1260
cgcaaaacac tacaaccccc aagcccagcg tggagggcca gcagccagca gcagctgctg     1320
cctgcgagcc cgtggaccac gcccagagtg agagcatcct gaaagtttcg cagcccagag     1380
ccctggagca gcaggcgtcc accccacccc caccccacc cccaccctg ctccctggtt     1440 ccagtgccga gccccctccc cctccccac caccccccct gcccagtgtg ggggctaagg     1500 cctcccaac agcaccccg ccccaccccc tgccaggcct gggggccatg gcccccccag     1560
cacctcctct accaccaccc ctgccaggct cctgtgagtt cctgccccca ccacctccac     1620
cactcccggg cttgggatgc ccgccccac cccaccccct gctgcctggt atgggctggg     1680
gccctcctcc acccccacct ccactactgc cctgcacctg cagccccccc gtggcgggag     1740
gcatggagga ggtcatcgtg gccaggtgg accatggctt gggctcagca tgggtcccca     1800
gccatcggcg ggtgaaccca cccacactgc gcatgaagaa gctgaactgg cagaagctgc     1860
catccaacgt ggcacgtgag cacaactcta tgtgggcgtc cctgagcagc cccgacgccg     1920
```

```
aggctgtgga gcccgacttc tccagcatcg agcgactatt ctccttccct gcagccaagc   1980
ccaaggagcc caccatggtg gccccccggg ccaggaagga gcccaaggag atcactttcc   2040
tcgatgccaa gaagagcctg aacctcaaca tcttcctgaa gcaatttaag tgctccaacg   2100
aggaggtcgc tgctatgatc cgggctggag ataccaccaa gtttgatgtg gaggttctca   2160
aacaactcct taagctcctt cccgagaagc acgagattga aaacctgcgg gcattcacag   2220
aggagcgagc caagctggcc agcgccgacc acttctacct cctcctgctg gccattccct   2280
gctaccagct gcgaatcgag tgcatgctgc tgtgtgaggg cgcggccgcc gtgctggaca   2340
tggtgcggcc caaggcccag ctggtgctgg ctgcctgcga aagcctgctc accagccgcc   2400
agctgcccat cttctgccag ctgatcctga aattgggaa cttcctcaac tacggcagcc   2460
acaccggtga cgccgacggc ttcaagatca gcacattgct gaagctcacg gagaccaagt   2520
cccagcagaa ccgcgtgacg ctgctgcacc acgtgctgga ggaagcggaa aagagccacc   2580
ccgacctcct gcagctgccc cgggacctgg aacagccctc gcaagcagca gggatcaacc   2640
tggagatcat ccgctcagag gccagctcca acctgaagaa gcttctggag accgagcgga   2700
aggtgtctgc ctccgtggcc gaggtccagg agcagtacac cgagcgcctc caggccagca   2760
tctcggcctt ccgggcactg gatgagctgt ttgaggccat cgagcagaag caacgggagc   2820
tggccgacta cctgtgtgag gacgcccagc agctgtccct ggaggacacg ttcagcacca   2880
tgaaggcttt ccgggacctt ttcctccgcg ccctgaagga gaacaaggac cggaaggagc   2940
aggcggcgaa ggcagagagg aggaagcagc agctggcgga ggaggaggcg cggcggcctc   3000
ggggagagga cggaagcct gtcaggaagg ggcccgggaa gcaggaggag gtgtgtgtca   3060
tcgatgccct gctggctgac atcaggaagg gcttccagct gcggaagaca gcccggggcc   3120
gcggggacac cgacgggggc agcaaggcag cctccatgga tcccccaaga gccacagagc   3180
ctgtggccac cagtaaccct gcaggagatc ccgtgggcag cacgcgctgt cccgcctctg   3240
agcccggcct tgatgctaca acagccagcg agtcccgggg ctgggacctt gtagacgccg   3300 tgaccccgg ccctcagccc accctggagc agttggagga gggtggtcca cggcccctgg   3360
agaggcgttc ttcctggtat gtggatgcca gcgatgtcct aaccactgag gatccccagt   3420
gcccccagcc cttggagggg gcctggccgg tgactctggg agatgctcag gccctgaagc   3480
ccctcaagtt ctccagcaac cagccccctg cagccggaag ttcaaggcaa gatgccaagg   3540
atcccacgtc cttgctgggc gtcctccagg ccgaggccga cagcacaagt gaggggctgg   3600
aggacgctgt ccacagccgt ggtgccgac ccctgcagc aggcccaggt ggggatgagg   3660
acgaggacga ggaggacacg gccccagagt ccgcactgga cacatccctg gacaagtcct   3720
tctccgagga tgcggtgacc gactcctcgg ggtcgggcac actccccagg gcccggggcc   3780
gggcctcaaa ggggaccggg aagcgaagga agaagcgtcc ctccaggagc caggaaggcc   3840
tcaggcccag gccaaggcc aagtgagaga gccaggcca caggacatgc tgccattctg   3900
ccaagagagg ctcttctggg ggccaggctg ggactgggcc ccggaaacca aaactccgtg   3960
ccttacccag ccggggccct cctggagcct tcttggggtg ttgtggctgg aacccgaca   4020 ggcaccagtg ccctgccagg cctggtgccc tcctggaccg cctgcacgtg ccagcctccc   4080
acctgcttcc taaaggcaac cctggcccac accgcatgc gcccggtgca gcctgccaag   4140
ggccagtcgg ggggtgctgc gtcctgccag tgtccaccac agctctgcct gcccttcagc   4200
ccagcaaggt ttaatcaaaa tgcaatgctt tgcaagtctt tactgcttgg aggtggctga   4260
```

-continued

```
gttgggggcc ctgggcaggg gtaagctggc aggcagtgcc atggcaggcc agggtcccct    4320
cccatggggt ctggccccg ttccagcatg tccagcccct gaagttggag tggggggcgg    4380
tctgcctttg ctgccactgc caggcctctg ccctgcagct gaaacttggc catcacatca    4440
acagaaaacc cctcccagtg ccagctgccc agcgtgggca ggccctgggg acaatacagg    4500
tccacctgag gggctgcagg gtgacaccca gcagccgctg ccccctcact gcccacccag    4560
cgagggcagc ctaccgagc ctgccccctg ccaggtgtgt gccctgaggc tggcggctgg    4620
atgcgtggcc aataaaaagc agacctagcc cggaaaaaaa aaaaaaaa                 4668
```

<210> SEQ ID NO 11
<211> LENGTH: 1240
<212> TYPE: PRT
<213> ORGANISM: Homo sapiens

<400> SEQUENCE: 11

```
Met Ser Val Lys Glu Gly Ala Gln Arg Lys Trp Ala Ala Leu Lys Glu
1               5                   10                  15

Lys Leu Gly Pro Gln Asp Ser Asp Pro Thr Glu Ala Asn Leu Glu Ser
            20                  25                  30

Ala Asp Pro Glu Leu Cys Ile Arg Leu Leu Gln Met Pro Ser Val Val
        35                  40                  45

Asn Tyr Ser Gly Leu Arg Lys Arg Leu Glu Gly Ser Asp Gly Gly Trp
    50                  55                  60

Met Val Gln Phe Leu Glu Gln Ser Gly Leu Asp Leu Leu Glu Ala
65                  70                  75                  80

Leu Ala Arg Leu Ser Gly Arg Gly Val Ala Arg Ile Ser Asp Ala Leu
                85                  90                  95

Leu Gln Leu Thr Cys Val Ser Cys Val Arg Ala Val Met Asn Ser Arg
            100                 105                 110

Gln Gly Ile Glu Tyr Ile Leu Ser Asn Gln Gly Tyr Val Arg Gln Leu
        115                 120                 125

Ser Gln Ala Leu Asp Thr Ser Asn Val Met Val Lys Lys Gln Val Phe
    130                 135                 140

Glu Leu Leu Ala Ala Leu Cys Ile Tyr Ser Pro Glu Gly His Val Leu
145                 150                 155                 160

Thr Leu Asp Ala Leu Asp His Tyr Lys Thr Val Cys Ser Gln Gln Tyr
                165                 170                 175

Arg Phe Ser Ile Val Met Asn Glu Leu Ser Gly Ser Asp Asn Val Pro
            180                 185                 190

Tyr Val Val Thr Leu Leu Ser Val Ile Asn Ala Val Ile Leu Gly Pro
        195                 200                 205

Glu Asp Leu Arg Ala Arg Thr Gln Leu Arg Asn Glu Phe Ile Gly Leu
    210                 215                 220

Gln Leu Leu Asp Val Leu Ala Arg Leu Arg Asp Leu Glu Asp Ala Asp
225                 230                 235                 240

Leu Leu Ile Gln Leu Glu Ala Phe Glu Glu Ala Lys Ala Glu Asp Glu
                245                 250                 255

Glu Glu Leu Leu Arg Val Ser Gly Gly Val Asp Met Ser Ser His Gln
            260                 265                 270

Glu Val Phe Ala Ser Leu Phe His Lys Val Ser Cys Ser Pro Val Ser
        275                 280                 285

Ala Gln Leu Leu Ser Val Leu Gln Gly Leu Leu His Leu Glu Pro Thr
    290                 295                 300
```

-continued

```
Leu Arg Ser Ser Gln Leu Leu Trp Glu Ala Leu Glu Ser Leu Val Asn
305                 310                 315                 320

Arg Ala Val Leu Leu Ala Ser Asp Ala Gln Glu Cys Thr Leu Glu Glu
                325                 330                 335

Val Val Glu Arg Leu Leu Ser Val Lys Gly Arg Pro Arg Pro Ser Pro
            340                 345                 350

Leu Val Lys Ala His Lys Ser Val Gln Ala Asn Leu Asp Gln Ser Gln
        355                 360                 365

Arg Gly Ser Ser Pro Gln Asn Thr Thr Thr Pro Lys Pro Ser Val Glu
370                 375                 380

Gly Gln Gln Pro Ala Ala Ala Ala Cys Glu Pro Val Asp His Ala
385                 390                 395                 400

Gln Ser Glu Ser Ile Leu Lys Val Ser Gln Pro Arg Ala Leu Glu Gln
                405                 410                 415

Gln Ala Ser Thr Pro Pro Pro Pro Pro Pro Pro Leu Leu Pro Gly
                420                 425                 430

Ser Ser Ala Glu Pro Pro Pro Pro Pro Pro Pro Pro Leu Pro Ser
            435                 440                 445

Val Gly Ala Lys Ala Leu Pro Thr Ala Pro Pro Pro Pro Leu Pro
450                 455                 460

Gly Leu Gly Ala Met Ala Pro Pro Ala Pro Pro Leu Pro Pro Leu
465                 470                 475                 480

Pro Gly Ser Cys Glu Phe Leu Pro Pro Pro Pro Pro Leu Pro Gly
                485                 490                 495

Leu Gly Cys Pro Pro Pro Pro Pro Leu Leu Pro Gly Met Gly Trp
            500                 505                 510

Gly Pro Pro Pro Pro Pro Pro Leu Leu Pro Cys Thr Cys Ser Pro
            515                 520                 525

Pro Val Ala Gly Gly Met Glu Glu Val Ile Val Ala Gln Val Asp His
530                 535                 540

Gly Leu Gly Ser Ala Trp Val Pro Ser His Arg Val Asn Pro Pro
545                 550                 555                 560

Thr Leu Arg Met Lys Lys Leu Asn Trp Gln Lys Leu Pro Ser Asn Val
                565                 570                 575

Ala Arg Glu His Asn Ser Met Trp Ala Ser Leu Ser Ser Pro Asp Ala
            580                 585                 590

Glu Ala Val Glu Pro Asp Phe Ser Ser Ile Glu Arg Leu Phe Ser Phe
        595                 600                 605

Pro Ala Ala Lys Pro Lys Glu Pro Thr Met Val Ala Pro Arg Ala Arg
610                 615                 620

Lys Glu Pro Lys Glu Ile Thr Phe Leu Asp Ala Lys Lys Ser Leu Asn
625                 630                 635                 640

Leu Asn Ile Phe Leu Lys Gln Phe Lys Cys Ser Asn Glu Glu Val Ala
                645                 650                 655

Ala Met Ile Arg Ala Gly Asp Thr Thr Lys Phe Asp Val Glu Val Leu
            660                 665                 670

Lys Gln Leu Leu Lys Leu Leu Pro Glu Lys His Glu Ile Glu Asn Leu
        675                 680                 685

Arg Ala Phe Thr Glu Glu Arg Ala Lys Leu Ala Ser Ala Asp His Phe
690                 695                 700

Tyr Leu Leu Leu Leu Ala Ile Pro Cys Tyr Gln Leu Arg Ile Glu Cys
705                 710                 715                 720

Met Leu Leu Cys Glu Gly Ala Ala Ala Val Leu Asp Met Val Arg Pro
```

```
                725                 730                 735
Lys Ala Gln Leu Val Leu Ala Ala Cys Glu Ser Leu Leu Thr Ser Arg
            740                 745                 750
Gln Leu Pro Ile Phe Cys Gln Leu Ile Leu Arg Ile Gly Asn Phe Leu
            755                 760                 765
Asn Tyr Gly Ser His Thr Gly Asp Ala Asp Gly Phe Lys Ile Ser Thr
            770                 775                 780
Leu Leu Lys Leu Thr Glu Thr Lys Ser Gln Gln Asn Arg Val Thr Leu
785                 790                 795                 800
Leu His His Val Leu Glu Glu Ala Glu Lys Ser His Pro Asp Leu Leu
                805                 810                 815
Gln Leu Pro Arg Asp Leu Glu Gln Pro Ser Gln Ala Ala Gly Ile Asn
            820                 825                 830
Leu Glu Ile Ile Arg Ser Glu Ala Ser Ser Asn Leu Lys Lys Leu Leu
            835                 840                 845
Glu Thr Glu Arg Lys Val Ser Ala Ser Val Ala Glu Val Gln Glu Gln
            850                 855                 860
Tyr Thr Glu Arg Leu Gln Ala Ser Ile Ser Ala Phe Arg Ala Leu Asp
865                 870                 875                 880
Glu Leu Phe Glu Ala Ile Glu Gln Lys Gln Arg Glu Leu Ala Asp Tyr
                885                 890                 895
Leu Cys Glu Asp Ala Gln Gln Leu Ser Leu Glu Asp Thr Phe Ser Thr
            900                 905                 910
Met Lys Ala Phe Arg Asp Leu Phe Leu Arg Ala Leu Lys Glu Asn Lys
            915                 920                 925
Asp Arg Lys Glu Gln Ala Ala Lys Ala Glu Arg Arg Lys Gln Gln Leu
        930                 935                 940
Ala Glu Glu Glu Ala Arg Arg Pro Arg Gly Asp Gly Lys Pro Val
945                 950                 955                 960
Arg Lys Gly Pro Gly Lys Gln Glu Glu Val Cys Val Ile Asp Ala Leu
                965                 970                 975
Leu Ala Asp Ile Arg Lys Gly Phe Gln Leu Arg Lys Thr Ala Arg Gly
            980                 985                 990
Arg Gly Asp Thr Asp Gly Gly Ser Lys Ala Ala Ser Met Asp Pro Pro
        995                 1000                1005
Arg Ala Thr Glu Pro Val Ala Thr Ser Asn Pro Ala Gly Asp Pro Val
        1010                1015                1020
Gly Ser Thr Arg Cys Pro Ala Ser Glu Pro Gly Leu Asp Ala Thr Thr
1025                1030                1035                1040
Ala Ser Glu Ser Arg Gly Trp Asp Leu Val Asp Ala Val Thr Pro Gly
            1045                1050                1055
Pro Gln Pro Thr Leu Glu Gln Leu Glu Gly Gly Pro Arg Pro Leu
        1060                1065                1070
Glu Arg Arg Ser Ser Trp Tyr Val Asp Ala Ser Asp Val Leu Thr Thr
        1075                1080                1085
Glu Asp Pro Gln Cys Pro Gln Pro Leu Glu Gly Ala Trp Pro Val Thr
        1090                1095                1100
Leu Gly Asp Ala Gln Ala Leu Lys Pro Lys Phe Ser Ser Asn Gln
1105                1110                1115                1120
Pro Pro Ala Ala Gly Ser Ser Arg Gln Asp Ala Lys Asp Pro Thr Ser
            1125                1130                1135
Leu Leu Gly Val Leu Gln Ala Glu Ala Asp Ser Thr Ser Glu Gly Leu
            1140                1145                1150
```

Glu Asp Ala Val His Ser Arg Gly Ala Arg Pro Pro Ala Ala Gly Pro
            1155                1160                1165

Gly Gly Asp Glu Asp Glu Asp Glu Asp Thr Ala Pro Glu Ser Ala
        1170                1175                1180

Leu Asp Thr Ser Leu Asp Lys Ser Phe Ser Glu Asp Ala Val Thr Asp
1185                1190                1195                1200

Ser Ser Gly Ser Gly Thr Leu Pro Arg Ala Arg Gly Arg Ala Ser Lys
                1205                1210                1215

Gly Thr Gly Lys Arg Arg Lys Lys Arg Pro Ser Arg Ser Gln Glu Gly
            1220                1225                1230

Leu Arg Pro Arg Pro Lys Ala Lys
        1235                1240

<210> SEQ ID NO 12
<211> LENGTH: 7
<212> TYPE: PRT
<213> ORGANISM: Artificial Sequence
<220> FEATURE:
<223> OTHER INFORMATION: peptide fragment
<220> FEATURE:
<221> NAME/KEY: VARIANT
<222> LOCATION: 4
<223> OTHER INFORMATION: Xaa = L or R

<400> SEQUENCE: 12

Val Thr Leu Xaa Ser Val Ile
1               5

<210> SEQ ID NO 13
<211> LENGTH: 7
<212> TYPE: PRT
<213> ORGANISM: Artificial Sequence
<220> FEATURE:
<223> OTHER INFORMATION: peptide fragment
<220> FEATURE:
<221> NAME/KEY: VARIANT
<222> LOCATION: 4
<223> OTHER INFORMATION: Xaa = R  or W

<400> SEQUENCE: 13

Thr Gln Leu Xaa Asn Glu Phe
1               5

<210> SEQ ID NO 14
<211> LENGTH: 5
<212> TYPE: PRT
<213> ORGANISM: Artificial Sequence
<220> FEATURE:
<223> OTHER INFORMATION: peptide fragment
<220> FEATURE:
<221> NAME/KEY: VARIANT
<222> LOCATION: 3
<223> OTHER INFORMATION: Xaa = R or H

<400> SEQUENCE: 14

Arg Ala Xaa Thr Gln
1               5

<210> SEQ ID NO 15
<211> LENGTH: 6
<212> TYPE: PRT
<213> ORGANISM: Artificial Sequence
<220> FEATURE:
<223> OTHER INFORMATION: peptide fragment
<220> FEATURE:
<221> NAME/KEY: VARIANT -continued

```
<222> LOCATION: 3
<223> OTHER INFORMATION: Xaa = S or P

<400> SEQUENCE: 15

Glu Leu Xaa Gly Ser Asp
1               5

<210> SEQ ID NO 16
<211> LENGTH: 6
<212> TYPE: PRT
<213> ORGANISM: Artificial Sequence
<220> FEATURE:
<223> OTHER INFORMATION: peptide fragment
<220> FEATURE:
<221> NAME/KEY: VARIANT
<222> LOCATION: 4
<223> OTHER INFORMATION: Xaa = E or K

<400> SEQUENCE: 16

Val Met Asn Xaa Leu Ser
1               5

<210> SEQ ID NO 17
<211> LENGTH: 6
<212> TYPE: PRT
<213> ORGANISM: Artificial Sequence
<220> FEATURE:
<223> OTHER INFORMATION: peptide fragment
<220> FEATURE:
<221> NAME/KEY: VARIANT
<222> LOCATION: 3
<223> OTHER INFORMATION: Xaa = R or Q

<400> SEQUENCE: 17

Gln Leu Xaa Asn Glu Phe
1               5

<210> SEQ ID NO 18
<211> LENGTH: 6
<212> TYPE: PRT
<213> ORGANISM: Artificial Sequence
<220> FEATURE:
<223> OTHER INFORMATION: peptide fragment
<220> FEATURE:
<221> NAME/KEY: VARIANT
<222> LOCATION: 4
<223> OTHER INFORMATION: Xaa = E or K

<400> SEQUENCE: 18

Leu Arg Asn Xaa Phe Ile
1               5

<210> SEQ ID NO 19
<211> LENGTH: 5
<212> TYPE: PRT
<213> ORGANISM: Artificial Sequence
<220> FEATURE:
<223> OTHER INFORMATION: peptide fragment
<220> FEATURE:
<221> NAME/KEY: VARIANT
<222> LOCATION: 3
<223> OTHER INFORMATION: Xaa = L or P

<400> SEQUENCE: 19

Arg Leu Xaa Gln Met
1               5

<210> SEQ ID NO 20
<211> LENGTH: 1240
```

```
<212> TYPE: PRT
<213> ORGANISM: Homo sapiens
<220> FEATURE:
<221> NAME/KEY: VARIANT
<222> LOCATION: 42
<223> OTHER INFORMATION: Xaa = L or P
<220> FEATURE:
<221> NAME/KEY: VARIANT
<222> LOCATION: 184
<223> OTHER INFORMATION: Xaa = E or K
<220> FEATURE:
<221> NAME/KEY: VARIANT
<222> LOCATION: 186
<223> OTHER INFORMATION: Xaa = S or P
<220> FEATURE:
<221> NAME/KEY: VARIANT
<222> LOCATION: 198
<223> OTHER INFORMATION: Xaa = L or R
<220> FEATURE:
<221> NAME/KEY: VARIANT
<222> LOCATION: 214
<223> OTHER INFORMATION: Xaa = R or H
<220> FEATURE:
<221> NAME/KEY: VARIANT
<222> LOCATION: 218
<223> OTHER INFORMATION: Xaa = R, W, or Q
<220> FEATURE:
<221> NAME/KEY: VARIANT
<222> LOCATION: 220
<223> OTHER INFORMATION: Xaa = E or K

<400> SEQUENCE: 20

Met Ser Val Lys Glu Gly Ala Gln Arg Lys Trp Ala Ala Leu Lys Glu
1               5                   10                  15

Lys Leu Gly Pro Gln Asp Ser Asp Pro Thr Glu Ala Asn Leu Glu Ser
            20                  25                  30

Ala Asp Pro Glu Leu Cys Ile Arg Leu Xaa Gln Met Pro Ser Val Val
        35                  40                  45

Asn Tyr Ser Gly Leu Arg Lys Arg Leu Glu Gly Ser Asp Gly Gly Trp
    50                  55                  60

Met Val Gln Phe Leu Glu Gln Ser Gly Leu Asp Leu Leu Leu Glu Ala
65                  70                  75                  80

Leu Ala Arg Leu Ser Gly Arg Gly Val Ala Arg Ile Ser Asp Ala Leu
                85                  90                  95

Leu Gln Leu Thr Cys Val Ser Cys Val Arg Ala Val Met Asn Ser Arg
            100                 105                 110

Gln Gly Ile Glu Tyr Ile Leu Ser Asn Gln Gly Tyr Val Arg Gln Leu
        115                 120                 125

Ser Gln Ala Leu Asp Thr Ser Asn Val Met Val Lys Lys Gln Val Phe
    130                 135                 140

Glu Leu Leu Ala Ala Leu Cys Ile Tyr Ser Pro Glu Gly His Val Leu
145                 150                 155                 160

Thr Leu Asp Ala Leu Asp His Tyr Lys Thr Val Cys Ser Gln Gln Tyr
                165                 170                 175

Arg Phe Ser Ile Val Met Asn Xaa Leu Xaa Gly Ser Asp Asn Val Pro
            180                 185                 190

Tyr Val Val Thr Leu Xaa Ser Val Ile Asn Ala Val Ile Leu Gly Pro
        195                 200                 205

Glu Asp Leu Arg Ala Xaa Thr Gln Leu Xaa Asn Xaa Phe Ile Gly Leu
    210                 215                 220

Gln Leu Leu Asp Val Leu Ala Arg Leu Arg Asp Leu Glu Asp Ala Asp
225                 230                 235                 240

Leu Leu Ile Gln Leu Glu Ala Phe Glu Glu Ala Lys Ala Glu Asp Glu
```

```
                       245                 250                 255
        Glu Glu Leu Leu Arg Val Ser Gly Gly Val Asp Met Ser Ser His Gln
                    260                 265                 270

Glu Val Phe Ala Ser Leu Phe His Lys Val Ser Cys Ser Pro Val Ser
                    275                 280                 285

Ala Gln Leu Leu Ser Val Leu Gln Gly Leu Leu His Leu Glu Pro Thr
                    290                 295                 300

Leu Arg Ser Ser Gln Leu Leu Trp Glu Ala Leu Glu Ser Leu Val Asn
        305                 310                 315                 320

Arg Ala Val Leu Leu Ala Ser Asp Ala Gln Glu Cys Thr Leu Glu Glu
                        325                 330                 335

Val Val Glu Arg Leu Leu Ser Val Lys Gly Arg Pro Arg Pro Ser Pro
                        340                 345                 350

Leu Val Lys Ala His Lys Ser Val Gln Ala Asn Leu Asp Gln Ser Gln
                        355                 360                 365

Arg Gly Ser Ser Pro Gln Asn Thr Thr Thr Pro Lys Pro Ser Val Glu
                        370                 375                 380

Gly Gln Gln Pro Ala Ala Ala Ala Cys Glu Pro Val Asp His Ala
        385                 390                 395                 400

Gln Ser Glu Ser Ile Leu Lys Val Ser Gln Pro Arg Ala Leu Glu Gln
                        405                 410                 415

Gln Ala Ser Thr Pro Pro Pro Pro Pro Pro Pro Leu Leu Pro Gly
                        420                 425                 430

Ser Ser Ala Glu Pro Pro Pro Pro Pro Pro Pro Pro Leu Pro Ser
                        435                 440                 445

Val Gly Ala Lys Ala Leu Pro Thr Ala Pro Pro Pro Pro Leu Pro
                450                 455                 460

Gly Leu Gly Ala Met Ala Pro Pro Ala Pro Leu Pro Pro Pro Leu
        465                 470                 475                 480

Pro Gly Ser Cys Glu Phe Leu Pro Pro Pro Pro Pro Leu Pro Gly
                        485                 490                 495

Leu Gly Cys Pro Pro Pro Pro Pro Leu Leu Pro Gly Met Gly Trp
                    500                 505                 510

Gly Pro Pro Pro Pro Pro Pro Leu Leu Pro Cys Thr Cys Ser Pro
                    515                 520                 525

Pro Val Ala Gly Gly Met Glu Glu Val Ile Val Ala Gln Val Asp His
                    530                 535                 540

Gly Leu Gly Ser Ala Trp Val Pro Ser His Arg Arg Val Asn Pro Pro
        545                 550                 555                 560

Thr Leu Arg Met Lys Lys Leu Asn Trp Gln Lys Leu Pro Ser Asn Val
                        565                 570                 575

Ala Arg Glu His Asn Ser Met Trp Ala Ser Leu Ser Ser Pro Asp Ala
                        580                 585                 590

Glu Ala Val Glu Pro Asp Phe Ser Ser Ile Glu Arg Leu Phe Ser Phe
                        595                 600                 605

Pro Ala Ala Lys Pro Lys Glu Pro Thr Met Val Ala Pro Arg Ala Arg
                        610                 615                 620

Lys Glu Pro Lys Glu Ile Thr Phe Leu Asp Ala Lys Lys Ser Leu Asn
        625                 630                 635                 640

Leu Asn Ile Phe Leu Lys Gln Phe Lys Cys Ser Asn Glu Glu Val Ala
                        645                 650                 655

Ala Met Ile Arg Ala Gly Asp Thr Thr Lys Phe Asp Val Glu Val Leu
                    660                 665                 670
```

```
Lys Gln Leu Leu Lys Leu Leu Pro Glu Lys His Glu Ile Glu Asn Leu
        675                 680                 685
Arg Ala Phe Thr Glu Glu Ala Lys Leu Ala Ser Ala Asp His Phe
        690                 695                 700
Tyr Leu Leu Leu Ala Ile Pro Cys Tyr Gln Leu Arg Ile Glu Cys
705                 710                 715                 720
Met Leu Leu Cys Glu Gly Ala Ala Val Leu Asp Met Val Arg Pro
                725                 730                 735
Lys Ala Gln Leu Val Leu Ala Ala Cys Glu Ser Leu Leu Thr Ser Arg
        740                 745                 750
Gln Leu Pro Ile Phe Cys Gln Leu Ile Leu Arg Ile Gly Asn Phe Leu
        755                 760                 765
Asn Tyr Gly Ser His Thr Gly Asp Ala Asp Gly Phe Lys Ile Ser Thr
770                 775                 780
Leu Leu Lys Leu Thr Glu Thr Lys Ser Gln Gln Asn Arg Val Thr Leu
785                 790                 795                 800
Leu His His Val Leu Glu Ala Glu Lys Ser His Pro Asp Leu Leu
        805                 810                 815
Gln Leu Pro Arg Asp Leu Glu Gln Pro Ser Gln Ala Ala Gly Ile Asn
        820                 825                 830
Leu Glu Ile Ile Arg Ser Glu Ala Ser Ser Asn Leu Lys Lys Leu Leu
        835                 840                 845
Glu Thr Glu Arg Lys Val Ser Ala Ser Val Ala Glu Val Gln Glu Gln
        850                 855                 860
Tyr Thr Glu Arg Leu Gln Ala Ser Ile Ser Ala Phe Arg Ala Leu Asp
865                 870                 875                 880
Glu Leu Phe Glu Ala Ile Glu Gln Lys Gln Arg Glu Leu Ala Asp Tyr
                885                 890                 895
Leu Cys Glu Asp Ala Gln Gln Leu Ser Leu Glu Asp Thr Phe Ser Thr
                900                 905                 910
Met Lys Ala Phe Arg Asp Leu Phe Leu Arg Ala Leu Lys Glu Asn Lys
        915                 920                 925
Asp Arg Lys Glu Gln Ala Ala Lys Ala Glu Arg Lys Gln Gln Leu
        930                 935                 940
Ala Glu Glu Glu Ala Arg Arg Pro Arg Gly Glu Asp Gly Lys Pro Val
945                 950                 955                 960
Arg Lys Gly Pro Gly Lys Gln Glu Glu Val Cys Val Ile Asp Ala Leu
                965                 970                 975
Leu Ala Asp Ile Arg Lys Gly Phe Gln Leu Arg Lys Thr Ala Arg Gly
                980                 985                 990
Arg Gly Asp Thr Asp Gly Gly Ser Lys Ala Ala Ser Met Asp Pro Pro
        995                 1000                1005
Arg Ala Thr Glu Pro Val Ala Thr Ser Asn Pro Ala Gly Asp Pro Val
1010                1015                1020
Gly Ser Thr Arg Cys Pro Ala Ser Glu Pro Gly Leu Asp Ala Thr Thr
1025                1030                1035                1040
Ala Ser Glu Ser Arg Gly Trp Asp Leu Val Asp Ala Val Thr Pro Gly
                1045                1050                1055
Pro Gln Pro Thr Leu Glu Gln Leu Glu Glu Gly Gly Pro Arg Pro Leu
                1060                1065                1070
Glu Arg Arg Ser Ser Trp Tyr Val Asp Ala Ser Asp Val Leu Thr Thr
        1075                1080                1085
```

```
Glu Asp Pro Gln Cys Pro Gln Pro Leu Glu Gly Ala Trp Pro Val Thr
    1090                1095                1100
Leu Gly Asp Ala Gln Ala Leu Lys Pro Leu Lys Phe Ser Ser Asn Gln
1105                1110                1115                1120
Pro Pro Ala Ala Gly Ser Ser Arg Gln Asp Ala Lys Asp Pro Thr Ser
            1125                1130                1135
Leu Leu Gly Val Leu Gln Ala Glu Ala Asp Ser Thr Ser Glu Gly Leu
        1140                1145                1150
Glu Asp Ala Val His Ser Arg Gly Ala Arg Pro Pro Ala Ala Gly Pro
    1155                1160                1165
Gly Gly Asp Glu Asp Glu Asp Glu Glu Asp Thr Ala Pro Glu Ser Ala
    1170                1175                1180
Leu Asp Thr Ser Leu Asp Lys Ser Phe Ser Glu Asp Ala Val Thr Asp
1185                1190                1195                1200
Ser Ser Gly Ser Gly Thr Leu Pro Arg Ala Arg Gly Arg Ala Ser Lys
                1205                1210                1215
Gly Thr Gly Lys Arg Arg Lys Arg Pro Ser Arg Ser Gln Glu Gly
    1220                1225                1230
Leu Arg Pro Arg Pro Lys Ala Lys
        1235                1240

<210> SEQ ID NO 21
<211> LENGTH: 4725
<212> TYPE: DNA
<213> ORGANISM: Homo sapiens
<220> FEATURE:
<221> NAME/KEY: variation
<222> LOCATION: 268
<223> OTHER INFORMATION: n = t or c
<220> FEATURE:
<221> NAME/KEY: variation
<222> LOCATION: 693
<223> OTHER INFORMATION: n = a or g
<220> FEATURE:
<221> NAME/KEY: variation
<222> LOCATION: 699
<223> OTHER INFORMATION: n = t or c
<220> FEATURE:
<221> NAME/KEY: variation
<222> LOCATION: 736
<223> OTHER INFORMATION: n = t or g
<220> FEATURE:
<221> NAME/KEY: variation
<222> LOCATION: 784
<223> OTHER INFORMATION: n = g or a
<220> FEATURE:
<221> NAME/KEY: variation
<222> LOCATION: 795
<223> OTHER INFORMATION: n = c or t
<220> FEATURE:
<221> NAME/KEY: variation
<222> LOCATION: (796)...(0)
<223> OTHER INFORMATION: n = g or a
<220> FEATURE:
<221> NAME/KEY: variation
<222> LOCATION: (801)...(0)
<223> OTHER INFORMATION: n = a or g

<400> SEQUENCE: 21
cgccccgcgc cgccaggag ccaccgtccg agccttgcgg agcgcggcag tgggcgccgg    60
ctgcccgcag ccctgaccc ggccccggac ggagcgccgg ccgcaccacc gccctctggc   120
cgttgcctca ccggctcggc aagatgtcg tgaaggaggg cgcacagcgc aagtgggcag   180
cgctgaagga gaaagctgggg ccacaggatt cggaccccac ggaggccaac ctggagagcg   240
cggaccccga gctgtgcatc cggctgcncc agatgccctc tgtggtcaac tactccggcc   300
```

-continued

```
tgcgcaagcg cctggagggc agcgacggcg gctggatggt gcagttcctg gagcagagcg    360
gcctggacct gctgctggag gcgctggcgc ggctgtcggg ccgcggcgtt gcacgtatct    420
ccgacgccct gctgcagctc acctgcgtca gctgcgtgcg cgccgtcatg aactcgcggc    480
agggcatcga gtacatcctc agcaaccagg gctacgtgcg ccagctctcc caggccctgg    540
acacatccaa cgtgatggtg aagaagcagg tgtttgagct actggctgcc ctgtgcatct    600
actctcccga gggccacgtg ctgaccctgg acgccctgga ccactacaag acggtgtgca    660
gccagcagta ccgcttcagc attgtcatga acnagctcnc cggcagcgac aacgtgccct    720
acgtggtcac cctgcntagc gtgatcaacg ccgtcatctt gggccccgag gacctgcgcg    780
cgcncaccca gctgnngaac nagtttatcg ggctgcagct gctggacgtc ctggctcgcc    840
tgcgagacct ggaggatgcc gacctgctga tccagctgga ggctttcgag gaggctaagg    900
ccgaggacga ggaggagctg ctgcgagtct ctggcggggt cgacatgagc agccaccagg    960
aggtctttgc ctccctgttc cacaaggtga gctgctcccc ggtgtctgcc cagctcctgt   1020
cggtgctgca gggcctcctg cacctggagc ccaccctccg ctccagccag ctgctctggg   1080
aggccctgga gagcctcgtg aaccgggccg tgctcctggc cagcgatgcc caggaatgca   1140
ccctggagga agtggttgag cggctcctgt ctgtcaaggg gcgacccaga ccgagccccc   1200
tggtcaaggc ccataaaagc gtccaggcca acctagacca gagccagagg ggcagctccc   1260
cgcaaaacac tacaaccccc aagcccagcg tggagggcca gcagccagca gcagctgctg   1320
cctgcgagcc cgtggaccac gcccagagtg agagcatcct gaaagtttcg cagcccagag   1380
ccctggagca gcaggcgtcc accccacccc caccccacc cccaccccctg ctccctggtt   1440
ccagtgccga gcccctccc cctccccac caccccccct gcccagtgtg ggggctaagg   1500
ccctcccaac agcaccccg ccccaccc tgccaggcct gggggccatg gcccccccag   1560
cacctcctct accaccaccc ctgccaggct cctgtgagtt cctgccccca ccacctccac   1620
cactcccggg cttgggatgc ccgccccac ccccaccct gctgcctggt atgggctggg   1680
gccctcctcc accccacct ccactactgc cctgcacctg cagcccccc gtggcgggag   1740
gcatggagga ggtcatcgtg gcccaggtgg accatggctt gggctcagca tgggtccccca   1800
gccatcggcg ggtgaaccca cccacactgc gcatgaagaa gctgaactgg cagaagctgc   1860
catccaacgt ggcacgtgag cacaactcta tgtgggcgtc cctgagcagc cccgacgccg   1920
aggctgtgga gcccgacttc tccagcatcg agcgactatt ctccttccct gcagccaagc   1980
ccaaggagcc caccatggtg gcccccgggc caggaaggaa gcccaaggag atcactttcc   2040
tcgatgccaa gaagagcctg aacctcaaca tcttcctgaa gcaatttaag tgctccaacg   2100
aggaggtcgc tgctatgatc cgggctggag ataccaccaa gtttgatgtg gaggttctca   2160
aacaactcct taagctcctt cccgagaagc acgagattga aaacctgcgg gcattcacag   2220
aggagcgagc caagctggcc agcgccgacc acttctacct cctcctgctg ccattccct   2280
gctaccagct gcgaatcgag tgcatgctgc tgtgtgaggg cgcggccgcc gtgctggaca   2340
tggtgcggcc caaggcccag ctggtgctgg ctgcctgcga aagcctgctc accagccgcc   2400
agctgccat cttctgccag ctgatcctga gaattgggaa cttcctcaac tacggcagcc   2460
acaccggtga cgccgacggc ttcaagatca gcacattgct gaagctcacg gagaccaagt   2520
cccagcagaa ccgcgtgacg ctgctgcacc acgtgctgga ggaagcggaa aagagccacc   2580
ccgacctcct gcagctgccc cgggacctgg aacagccctc gcaagcagca gggatcaacc   2640
```

```
tggagatcat ccgctcagag gccagctcca acctgaagaa gcttctggag accgagcgga    2700
aggtgtctgc ctccgtggcc gaggtccagg agcagtacac cgagcgcctc caggccagca    2760
tctcggcctt ccgggcactg gatgagctgt tgaggccat cgagcagaag caacgggagc     2820
tggccgacta cctgtgtgag gacgccagc agctgtccct ggaggacacg ttcagcacca     2880
tgaaggcttt ccgggacctt ttcctccgcg ccctgaagga gaacaaggac cggaaggagc    2940
aggcggcgaa ggcagagagg aggaagcagc agctggcgga ggaggaggcg cggcggcctc    3000
ggggagagga cgggaagcct gtcaggaagg ggcccgggaa gcaggaggag gtgtgtgtca    3060
tcgatgccct gctggctgac atcaggaagg gcttccagct gcggaagaca gcccggggcc    3120
gcggggacac cgacggggggc agcaaggcag cctccatgga tcccccaaga gccacagagc   3180
ctgtggccac cagtaaccct gcaggagatc ccgtgggcag cacgcgctgt cccgcctctg    3240
agcccggcct tgatgctaca acagccagcg agtcccgggg ctgggacctt gtagacgccg    3300 tgaccccgg ccctcagccc acctggagc agttggagga gggtggtcca cggcccctgg      3360
agaggcgttc ttcctggtat gtggatgcca gcgatgtcct aaccactgag gatccccagt    3420 gccccccagcc cttggagggg gcctggccgg tgactctggg agatgctcag gccctgaagc   3480
ccctcaagtt ctccagcaac cagcccctg cagccggaag ttcaaggcaa gatgccaagg     3540
atcccacgtc cttgctgggc gtcctccagg ccgaggccga cagcacaagt gaggggctgg    3600
aggacgctgt ccacagccgt ggtgccagac cccctgcagc aggcccaggt ggggatgagg    3660
acgaggacga ggaggacacg gccccagagt ccgcactgga cacatccctg acaagtcct    3720 tctccgagga tgcggtgacc gactcctcgg ggtcgggcac actccccagg gcccggggcc    3780
gggcctcaaa ggggaccggg aagcgaagga agaagcgtcc ctccaggagc caggaagagg    3840 ttcccccctga ttctgatgat aataaaacaa agaaactgtg tgtgatccag taaggcctca   3900
ggcccaggcc caaggccaag tgagagagcc caggccacag acatgctgc cattctgcca    3960 agagaggctc ttctggggc caggctggga ctgggcccg gaaaccaaaa ctccgtgcct     4020
tacccagccg gggccctcct ggagccttct tggggtgttg tggctgggaa cccgacaggc    4080
accagtgccc tgccaggcct ggtgccctcc tggaccgcct gcacgtgcca gcctcccacc    4140
tgcttcctaa aggcaaccct ggcccacacc cgcatgcgcc cggtgcagcc tgccaagggc    4200
cagtcggggg gtgctgcgtc ctgccagtgt ccaccacagc tctgcctgcc cttcagccca    4260
gcaaggttta atcaaaatgc aatgctttgc aagtctttac tgcttggagg tggctgagtt    4320
gggggccctg gcaggggta agctggcagg cagtgccatg gcaggccagg gtcccctccc     4380
atggggtctg gcccccgttc cagcatgtcc agccctgaa gttggagtgg ggggcggtct     4440
gcctttgctg ccactgccag gcctctgccc tgcagctgaa acttggccat cacatcaaca    4500
gaaaacccct cccagtgcca gctgcccagc gtgggcaggc cctggggaca atacaggtcc    4560
acctgagggg ctgcagggtg acacccagca gccgctgccc cctcactgcc cacccagcga    4620
gggcagccta cccgagcctg cccctgcca ggtgtgtgcc ctgaggctgg cggctggatg     4680
cgtggccaat aaaaagcaga cctagcccgg aaaaaaaaaa aaaaa                    4725

<210> SEQ ID NO 22
<211> LENGTH: 57
<212> TYPE: PRT
<213> ORGANISM: Artificial Sequence
<220> FEATURE:
<223> OTHER INFORMATION: Protein fragment

<400> SEQUENCE: 22
```

```
Met Ser Val Lys Glu Gly Ala Gln Arg Lys Trp Ala Ala Leu Lys Glu
1               5                   10                  15

Lys Leu Gly Pro Gln Asp Ser Asp Pro Thr Glu Ala Asn Leu Glu Ser
            20                  25                  30

Ala Asp Pro Glu Leu Cys Ile Arg Leu Leu Gln Met Pro Ser Val Val
        35                  40                  45

Asn Tyr Ser Gly Leu Arg Lys Arg Leu
    50                  55
```

<210> SEQ ID NO 23
<211> LENGTH: 57
<212> TYPE: PRT
<213> ORGANISM: Artificial Sequence
<220> FEATURE:
<223> OTHER INFORMATION: Protein fragment

<400> SEQUENCE: 23

```
Met Ser Val Lys Glu Gly Ala Gln Arg Lys Trp Ala Ala Leu Lys Glu
1               5                   10                  15

Lys Leu Gly Pro Gln Asp Ser Asp Pro Thr Glu Ala Asn Leu Glu Ser
            20                  25                  30

Ala Glu Pro Glu Leu Cys Ile Arg Leu Leu Gln Met Pro Ser Val Val
        35                  40                  45

Asn Tyr Ser Gly Leu Arg Lys Arg Leu
    50                  55
```

<210> SEQ ID NO 24
<211> LENGTH: 57
<212> TYPE: PRT
<213> ORGANISM: Artificial Sequence
<220> FEATURE:
<223> OTHER INFORMATION: Protein fragment

<400> SEQUENCE: 24

```
Met Ser Val Lys Glu Gly Val Gln Lys Lys Trp Ala Ala Leu Lys Glu
1               5                   10                  15

Lys Leu Gly Pro Gln Asp Gly Asp Pro Thr Glu Ala Asn Leu Glu Asn
            20                  25                  30

Ala Glu Pro Glu Leu Cys Ile Arg Leu Leu Gln Met Pro Ser Val Val
        35                  40                  45

Asn Tyr Ser Gly Leu Arg Lys Arg Leu
    50                  55
```

<210> SEQ ID NO 25
<211> LENGTH: 60
<212> TYPE: PRT
<213> ORGANISM: Artificial Sequence
<220> FEATURE:
<223> OTHER INFORMATION: Protein fragment

<400> SEQUENCE: 25

```
Met Ser Met Lys Ala Glu Gly Ala Gln Gln Lys Trp Ala Ala Val Arg
1               5                   10                  15

Gly Arg Leu Gly Ser Ser Gln Asp Ser Asp Gly Pro Gln Glu Ala Asn
            20                  25                  30

Leu Glu Asn Ala Asp Ala Glu Leu Cys Ile Arg Leu Leu Gln Val Pro
        35                  40                  45

Ser Val Val Asn Tyr Ser Gly Leu Arg Lys Arg Leu
    50                  55                  60
```

<210> SEQ ID NO 26
<211> LENGTH: 60
<212> TYPE: PRT
<213> ORGANISM: Artificial Sequence
<220> FEATURE:
<223> OTHER INFORMATION: Protein fragment

<400> SEQUENCE: 26

Tyr Arg Phe Ser Ile Val Met Asn Glu Leu Ser Gly Ser Asp Asn Val
1               5                   10                  15

Pro Tyr Val Val Thr Leu Leu Ser Val Ile Asn Ala Val Ile Leu Gly
            20                  25                  30

Pro Glu Asp Leu Arg Ala Arg Thr Gln Leu Arg Asn Glu Phe Ile Gly
        35                  40                  45

Leu Gln Leu Leu Asp Val Leu Ala Arg Leu Arg Asp
    50                  55                  60

<210> SEQ ID NO 27
<211> LENGTH: 60
<212> TYPE: PRT
<213> ORGANISM: Artificial Sequence
<220> FEATURE:
<223> OTHER INFORMATION: Protein fragment

<400> SEQUENCE: 27

Tyr Arg Phe Ser Ile Val Met Asn Glu Leu Ser Gly Ser Asp Asn Val
1               5                   10                  15

Pro Tyr Val Val Thr Leu Leu Ser Val Ile Asn Ala Val Ile Leu Gly
            20                  25                  30

Pro Glu Asp Leu Arg Val Arg Thr Gln Leu Arg Asn Glu Phe Ile Gly
        35                  40                  45

Leu Gln Leu Leu Asp Val Leu Ala Arg Leu Arg Asp
    50                  55                  60

<210> SEQ ID NO 28
<211> LENGTH: 60
<212> TYPE: PRT
<213> ORGANISM: Artificial Sequence
<220> FEATURE:
<223> OTHER INFORMATION: Protein fragment

<400> SEQUENCE: 28

Tyr Arg Phe Ser Val Ile Met Ser Glu Leu Ser Asp Ser Asp Asn Val
1               5                   10                  15

Pro Tyr Val Val Thr Leu Leu Ser Val Ile Asn Ala Ile Ile Leu Gly
            20                  25                  30

Pro Glu Asp Leu Arg Ser Arg Ala Gln Leu Arg Ser Glu Phe Ile Gly
        35                  40                  45

Leu Gln Leu Leu Asp Ile Leu Thr Arg Leu Arg Asp
    50                  55                  60

<210> SEQ ID NO 29
<211> LENGTH: 60
<212> TYPE: PRT
<213> ORGANISM: Artificial Sequence
<220> FEATURE:
<223> OTHER INFORMATION: Protein fragment

<400> SEQUENCE: 29

Tyr Arg Phe Ser Val Ile Met Asn Glu Leu Ser Asp Ser Asp Asn Val
1               5                   10                  15

```
Pro Tyr Val Val Thr Leu Leu Ser Val Ile Asn Ala Leu Ile Leu Gly
            20                  25                  30

Pro Glu Asp Leu Arg Thr Arg Ala Gln Leu Arg Ser Glu Phe Ile Gly
            35                  40                  45

Leu Gln Leu Leu Asp Ile Leu Thr Arg Leu Arg Asp
50                  55                  60

<210> SEQ ID NO 30
<211> LENGTH: 60
<212> TYPE: PRT
<213> ORGANISM: Artificial Sequence
<220> FEATURE:
<223> OTHER INFORMATION: Protein fragment

<400> SEQUENCE: 30

Tyr Arg Phe Ser Val Ile Met Asn Glu Leu Ser Ser Thr Asp Asn Val
1               5                   10                  15

Pro Tyr Ile Ile Thr Leu Leu Ser Val Ile Asn Ala Ile Ile Leu Gly
            20                  25                  30

Thr Glu Glu Leu Arg Ala Arg Thr Gln Leu Arg Asn Glu Phe Ile Gly
            35                  40                  45

Leu Gln Leu Leu Asp Ile Leu Thr Lys Leu Arg Asp
50                  55                  60

<210> SEQ ID NO 31
<211> LENGTH: 60
<212> TYPE: PRT
<213> ORGANISM: Artificial Sequence
<220> FEATURE:
<223> OTHER INFORMATION: Protein fragment

<400> SEQUENCE: 31

Tyr Arg Phe Ser Val Ile Met Asn Glu Leu Arg Ser Thr Asp Asn Val
1               5                   10                  15

Pro Tyr Met Val Thr Leu Leu Ser Val Ile Asn Ala Leu Ile Phe Ser
            20                  25                  30

Ala Asp Gly Leu Gln Gln Arg Asp Lys Met Arg Lys Glu Phe Ile Gly
            35                  40                  45

Leu Gln Leu Leu Gln Leu Leu Pro Lys Leu Arg Glu
50                  55                  60

<210> SEQ ID NO 32
<211> LENGTH: 57
<212> TYPE: PRT
<213> ORGANISM: Homo sapiens

<400> SEQUENCE: 32

Met Ser Val Lys Glu Gly Ala Gln Arg Lys Trp Ala Ala Leu Lys Glu
1               5                   10                  15

Lys Leu Gly Pro Gln Asp Ser Asp Pro Thr Glu Ala Asn Leu Glu Ser
            20                  25                  30

Ala Asp Pro Glu Leu Cys Ile Arg Leu Leu Gln Met Pro Ser Val Val
            35                  40                  45

Asn Tyr Ser Gly Leu Arg Lys Arg Leu
            50                  55

<210> SEQ ID NO 33
<211> LENGTH: 57
<212> TYPE: PRT
<213> ORGANISM: Mus musculus
```

```
<400> SEQUENCE: 33

Met Ser Val Lys Glu Gly Ala Gln Arg Lys Trp Ala Ala Leu Lys Glu
1               5                   10                  15

Lys Leu Gly Pro Gln Asp Ser Asp Pro Thr Glu Ala Asn Leu Glu Ser
                20                  25                  30

Ala Glu Pro Glu Leu Cys Ile Arg Leu Leu Gln Met Pro Ser Val Val
            35                  40                  45

Asn Tyr Ser Gly Leu Arg Lys Arg Leu
    50                  55

<210> SEQ ID NO 34
<211> LENGTH: 57
<212> TYPE: PRT
<213> ORGANISM: Didelphis virginiana

<400> SEQUENCE: 34

Met Ser Val Lys Glu Gly Val Gln Lys Lys Trp Ala Ala Leu Lys Glu
1               5                   10                  15

Lys Leu Gly Pro Gln Asp Ser Asp Pro Thr Glu Ala Asn Leu Glu Asn
                20                  25                  30

Ala Glu Pro Glu Leu Cys Ile Arg Leu Leu Gln Met Pro Ser Val Val
            35                  40                  45

Asn Tyr Ser Gly Leu Arg Lys Arg Leu
    50                  55

<210> SEQ ID NO 35
<211> LENGTH: 60
<212> TYPE: PRT
<213> ORGANISM: Danio rerio

<400> SEQUENCE: 35

Met Ser Met Lys Ala Glu Gly Ala Gln Gln Lys Trp Ala Ala Val Arg
1               5                   10                  15

Gly Arg Leu Gly Ser Ser Gln Asp Ser Asp Gly Pro Gln Glu Ala Asn
                20                  25                  30

Leu Glu Asn Ala Asp Ala Glu Leu Cys Ile Arg Leu Leu Gln Val Pro
            35                  40                  45

Ser Val Val Asn Tyr Ser Gly Leu Arg Lys Arg Leu
    50                  55                  60

<210> SEQ ID NO 36
<211> LENGTH: 60
<212> TYPE: PRT
<213> ORGANISM: Homo sapiens

<400> SEQUENCE: 36

Tyr Arg Phe Ser Ile Val Met Asn Glu Leu Ser Gly Ser Asp Asn Val
1               5                   10                  15

Pro Tyr Val Val Thr Leu Leu Ser Val Ile Asn Ala Val Ile Leu Gly
                20                  25                  30

Pro Glu Asp Leu Arg Ala Arg Thr Gln Leu Arg Asn Glu Phe Ile Gly
            35                  40                  45

Leu Gln Leu Leu Asp Val Leu Ala Arg Leu Arg Asp
    50                  55                  60

<210> SEQ ID NO 37
<211> LENGTH: 60
<212> TYPE: PRT
<213> ORGANISM: Pan troglodytes
```

-continued

```
<400> SEQUENCE: 37

Tyr Arg Phe Ser Ile Val Met Asn Glu Leu Ser Gly Ser Asp Asn Val
1               5                   10                  15

Pro Tyr Val Val Thr Leu Leu Ser Val Ile Asn Ala Val Ile Leu Gly
            20                  25                  30

Pro Glu Asp Leu Arg Val Arg Thr Gln Leu Arg Asn Glu Phe Ile Gly
        35                  40                  45

Leu Gln Leu Leu Asp Val Leu Ala Arg Leu Arg Asp
    50                  55                  60

<210> SEQ ID NO 38
<211> LENGTH: 60
<212> TYPE: PRT
<213> ORGANISM: Mus musculus

<400> SEQUENCE: 38

Tyr Arg Phe Ser Val Ile Met Ser Glu Leu Ser Asp Ser Asp Asn Val
1               5                   10                  15

Pro Tyr Val Val Thr Leu Leu Ser Val Ile Asn Ala Ile Ile Leu Gly
            20                  25                  30

Pro Glu Asp Leu Arg Ser Arg Ala Gln Leu Arg Ser Glu Phe Ile Gly
        35                  40                  45

Leu Gln Leu Leu Asp Ile Leu Thr Arg Leu Arg Asp
    50                  55                  60

<210> SEQ ID NO 39
<211> LENGTH: 60
<212> TYPE: PRT
<213> ORGANISM: Rattus norvegicus

<400> SEQUENCE: 39

Tyr Arg Phe Ser Val Ile Met Ser Glu Leu Ser Asp Ser Asp Asn Val
1               5                   10                  15

Pro Tyr Val Val Thr Leu Leu Ser Val Ile Asn Ala Leu Ile Leu Gly
            20                  25                  30

Pro Glu Asp Leu Arg Thr Arg Ala Gln Leu Arg Ser Glu Phe Ile Gly
        35                  40                  45

Leu Gln Leu Leu Asp Ile Leu Thr Arg Leu Arg Asp
    50                  55                  60

<210> SEQ ID NO 40
<211> LENGTH: 60
<212> TYPE: PRT
<213> ORGANISM: Didelphis virginiana

<400> SEQUENCE: 40

Tyr Arg Phe Ser Val Ile Met Ser Glu Leu Ser Ser Thr Asp Asn Val
1               5                   10                  15

Pro Tyr Ile Ile Thr Leu Leu Ser Val Ile Asn Ala Ile Ile Leu Gly
            20                  25                  30

Thr Glu Glu Leu Arg Ala Arg Thr Gln Leu Arg Asn Glu Phe Ile Gly
        35                  40                  45

Leu Gln Leu Leu Asp Ile Leu Thr Lys Leu Arg Asp
    50                  55                  60

<210> SEQ ID NO 41
<211> LENGTH: 60
<212> TYPE: PRT
```

```
<213> ORGANISM: Danio rerio

<400> SEQUENCE: 41

Tyr Arg Phe Ser Val Ile Met Ser Glu Leu Ser Ser Thr Asp Asn Val
1               5                   10                  15

Pro Tyr Met Val Thr Leu Leu Ser Val Ile Asn Ala Leu Ile Phe Ser
            20                  25                  30

Ala Asp Gly Leu Gln Gln Arg Asp Lys Met Arg Lys Glu Phe Ile Gly
        35                  40                  45

Leu Gln Leu Leu Gln Leu Leu Pro Lys Leu Arg Glu
50                  55                  60
```